United States Patent
Luciano et al.

(10) Patent No.: US 8,665,507 B2
(45) Date of Patent: Mar. 4, 2014

(54) MODULE MOUNTING MIRROR ENDOSCOPY

(75) Inventors: Vincent Luciano, Shoreham, NY (US); Ron Goldman, Cold Spring Harbor, NY (US); Fred Wood, Medford, NY (US)

(73) Assignee: Accuvein, Inc.

( * ) Notice: Subject to any disclaimer, the term of this patent is extended or adjusted under 35 U.S.C. 154(b) by 464 days.

(21) Appl. No.: 12/925,742

(22) Filed: Oct. 28, 2010

(65) Prior Publication Data

US 2011/0118611 A1    May 19, 2011

Related U.S. Application Data

(63) Continuation-in-part of application No. 11/478,322, filed on Jun. 29, 2006, and a continuation-in-part of application No. 11/700,729, filed on Jan. 31, 2007, and a continuation-in-part of application No. 11/807,359, filed on May 25, 2007, and a continuation-in-part of application No. 12/215,713, filed on Jun. 27, 2008, and a continuation-in-part of application No. 11/823,862, filed on Jun. 28, 2007, now Pat. No. 7,983,738, and a continuation-in-part of application No. 12/804,506, filed on Jul. 22, 2010.

(60) Provisional application No. 61/279,980, filed on Oct. 28, 2009.

(51) Int. Cl.
G02B 26/08    (2006.01)

(52) U.S. Cl.
USPC ................. 359/224.1; 359/199.3; 359/199.4; 359/200.7; 359/200.8

(58) Field of Classification Search
USPC ..................... 359/196.1–226.2, 198.1–199.4, 359/200.6–200.8
See application file for complete search history.

(56) References Cited

U.S. PATENT DOCUMENTS 3,818,129 A    6/1974 Yamamoto
(Continued)

FOREIGN PATENT DOCUMENTS

FR    2289149    5/1976
GB    1507329    4/1978
(Continued)

OTHER PUBLICATIONS

Chris Wiklof, "Display Technology Spawns Laser Camera," LaserFocusWorld, Dec. 1, 2004, vol. 40, Issue 12, PennWell Corp., USA.

(Continued)

*Primary Examiner* — James Phan
(74) *Attorney, Agent, or Firm* — Thomas A. O'Rourke; Bodner & O'Rourke, LLP

(57)    ABSTRACT

The present invention is directed to a two-dimensional scanning arrangement for a laser vein-illumination device that includes a base and a frame connected to the base using at least one flexible hinge. The hinge allows the frame to move angularly with respect to the base in a first direction. The invention further includes a means for exciting angular oscillations of the frame at or near said frame's resonant frequency. An elastic torsional element having a proximal end rigidly attached to said frame and a distal end rigidly attached to a mirror is also included. The torsional element allows the mirror to move angularly with respect to the frame in a second direction, generally perpendicular to the first direction. There may also be a means for exciting the angular oscillations of the mirror.

The invention also includes a device for optically inspecting confined spaces having one or more small access orifices. The device includes at least one laser light source and a scanning means which scans one or more laser beam in a two-dimensional pattern over an inspection area. Also present is at least one light detector, sensitive to the light of the laser beam(s) being reflected from the inspection area. There is also a connecting member being thin and long enough to reach the inspection area through the access orifice.

19 Claims, 25 Drawing Sheets

(56) References Cited

U.S. PATENT DOCUMENTS

| | | |
|---|---|---|
| 2,289,149 A | 5/1976 | Siemens |
| 4,182,322 A | 1/1980 | Miller |
| 4,265,227 A | 5/1981 | Ruge |
| 4,312,357 A | 1/1982 | Andersson et al. |
| 4,321,930 A | 3/1982 | Jobsis et al. |
| 4,495,949 A | 1/1985 | Stoller |
| 4,502,075 A | 2/1985 | DeForest et al. |
| 4,619,249 A | 10/1986 | Landry |
| 4,817,622 A | 4/1989 | Pennypacker et al. |
| RE33,234 E | 6/1990 | Landry |
| 5,214,458 A | 5/1993 | Kanai |
| 5,261,581 A | 11/1993 | Harden |
| 5,406,070 A | 4/1995 | Edgar et al. |
| 5,423,091 A | 6/1995 | Lange |
| 5,519,208 A | 5/1996 | Esparza et al. |
| 5,541,820 A | 7/1996 | McLaughlin |
| 5,603,328 A | 2/1997 | Zucker et al. |
| 5,608,210 A | 3/1997 | Esparza et al. |
| 5,631,976 A | 5/1997 | Bolle et al. |
| 5,678,555 A | 10/1997 | O'Connell |
| 5,772,593 A | 6/1998 | Hakamata |
| 5,836,877 A | 11/1998 | Zavislan |
| 5,860,967 A | 1/1999 | Zavislan et al. |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Mannheimer et al. |
| 6,032,070 A | 2/2000 | Flock et al. |
| 6,056,692 A | 5/2000 | Schwartz |
| 6,061,583 A | 5/2000 | Shihara et al. |
| 6,135,599 A | 10/2000 | Fang |
| 6,149,644 A | 11/2000 | Xie |
| 6,178,340 B1 | 1/2001 | Svetliza |
| 6,230,046 B1 | 5/2001 | Crane et al. |
| 6,251,073 B1 | 6/2001 | Imran et al. |
| 6,263,227 B1 | 7/2001 | Boggett et al. |
| 6,334,850 B1 | 1/2002 | Amano et al. |
| 6,424,858 B1 | 7/2002 | Williams |
| 6,463,309 B1 | 10/2002 | Ilia |
| 6,464,646 B1 | 10/2002 | Shalom et al. |
| 6,542,246 B1 | 4/2003 | Toida |
| 6,556,854 B1 | 4/2003 | Sato et al. |
| 6,556,858 B1 | 4/2003 | Zeman |
| 6,648,227 B2 | 11/2003 | Swartz et al. |
| 6,689,075 B2 | 2/2004 | West |
| 6,690,964 B2 | 2/2004 | Bieger et al. |
| 6,702,749 B2 | 3/2004 | Paladini et al. |
| 6,782,161 B2 | 8/2004 | Barolet et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,980,852 B2 | 12/2005 | Jersey-Willuhn et al. |
| 7,158,660 B2 | 1/2007 | Gee, Jr. et al. |
| 7,225,005 B2 | 5/2007 | Kaufman et al. |
| 7,239,909 B2 | 7/2007 | Zeman |
| 7,247,832 B2 | 7/2007 | Webb |
| 7,283,181 B2 | 10/2007 | Allen |
| 7,333,213 B2 | 2/2008 | Kempe |
| 7,359,531 B2 | 4/2008 | Endoh et al. |
| 7,608,057 B2 | 10/2009 | Woehr et al. |
| 2002/0016533 A1 | 2/2002 | Marchitto |
| 2002/0118338 A1 | 8/2002 | Kohayakawa |
| 2003/0018271 A1 | 1/2003 | Kimble |
| 2004/0022421 A1 | 2/2004 | Endoh et al. |
| 2004/0237051 A1 | 8/2004 | Ogawa et al. |
| 2004/0171923 A1 | 9/2004 | Kalafut et al. |
| 2005/0017924 A1 | 1/2005 | Utt et al. |
| 2005/0043596 A1 | 2/2005 | Chance |
| 2005/0047134 A1 | 3/2005 | Mueller et al. |
| 2005/0113650 A1 | 5/2005 | Pacione et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1* | 7/2005 | Turner et al. ............... 359/224 |
| 2005/0157939 A1 | 7/2005 | Arsenault et al. |
| 2005/0161051 A1 | 7/2005 | Pankratov et al. |
| 2005/0174777 A1 | 8/2005 | Cooper et al. |
| 2005/0175048 A1 | 8/2005 | Stern et al. |
| 2005/0215875 A1 | 9/2005 | Khou |
| 2005/0281445 A1 | 12/2005 | Marcotte et al. |
| 2006/0025679 A1 | 2/2006 | Viswanathan et al. |
| 2006/0081252 A1 | 4/2006 | Wood |
| 2006/0103811 A1 | 5/2006 | May et al. |
| 2006/0122515 A1 | 6/2006 | Zeman |
| 2006/0129037 A1 | 6/2006 | Kaufman et al. |
| 2006/0129038 A1 | 6/2006 | Zelenchuk et al. |
| 2006/0173351 A1 | 8/2006 | Marcotte et al. |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2007/0016079 A1 | 1/2007 | Freeman et al. |
| 2007/0115435 A1 | 5/2007 | Rosendaal |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2010/0051808 A1 | 3/2010 | Zeman et al. |
| 2010/0087787 A1 | 4/2010 | Woehr et al. |
| 2010/0177184 A1 | 7/2010 | Berryhill et al. |
| 2010/0312120 A1 | 12/2010 | Meier |

FOREIGN PATENT DOCUMENTS

| | | |
|---|---|---|
| JP | 08023501 A | 1/1996 |
| JP | 2002328428 A | 11/2002 |
| JP | 2004237051 | 8/2004 |
| WO | WO 94/22370 | 10/1994 |
| WO | WO 96/39925 | 12/1996 |
| WO | WO 9826583 | 6/1998 |
| WO | WO 01/82786 | 11/2001 |
| WO | WO 03/009750 | 2/2003 |
| WO | 2007/078447 | 7/2007 |

OTHER PUBLICATIONS

Nikbin, Darius, "IPMS Targets Colour Laser Projectors," Optics & Laser Europe, Mar. 2006, Issue 137, p. 11.

* cited by examiner

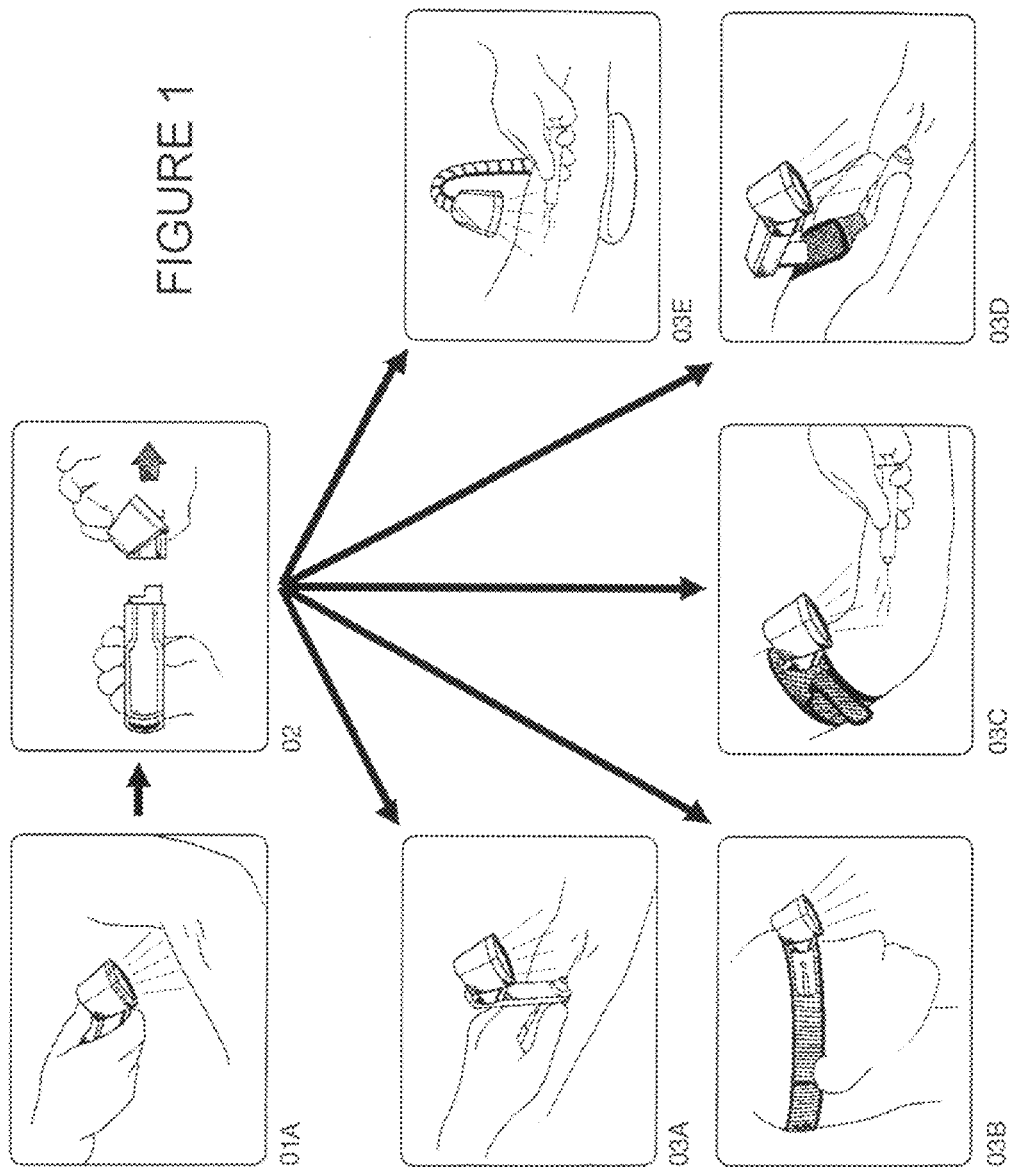

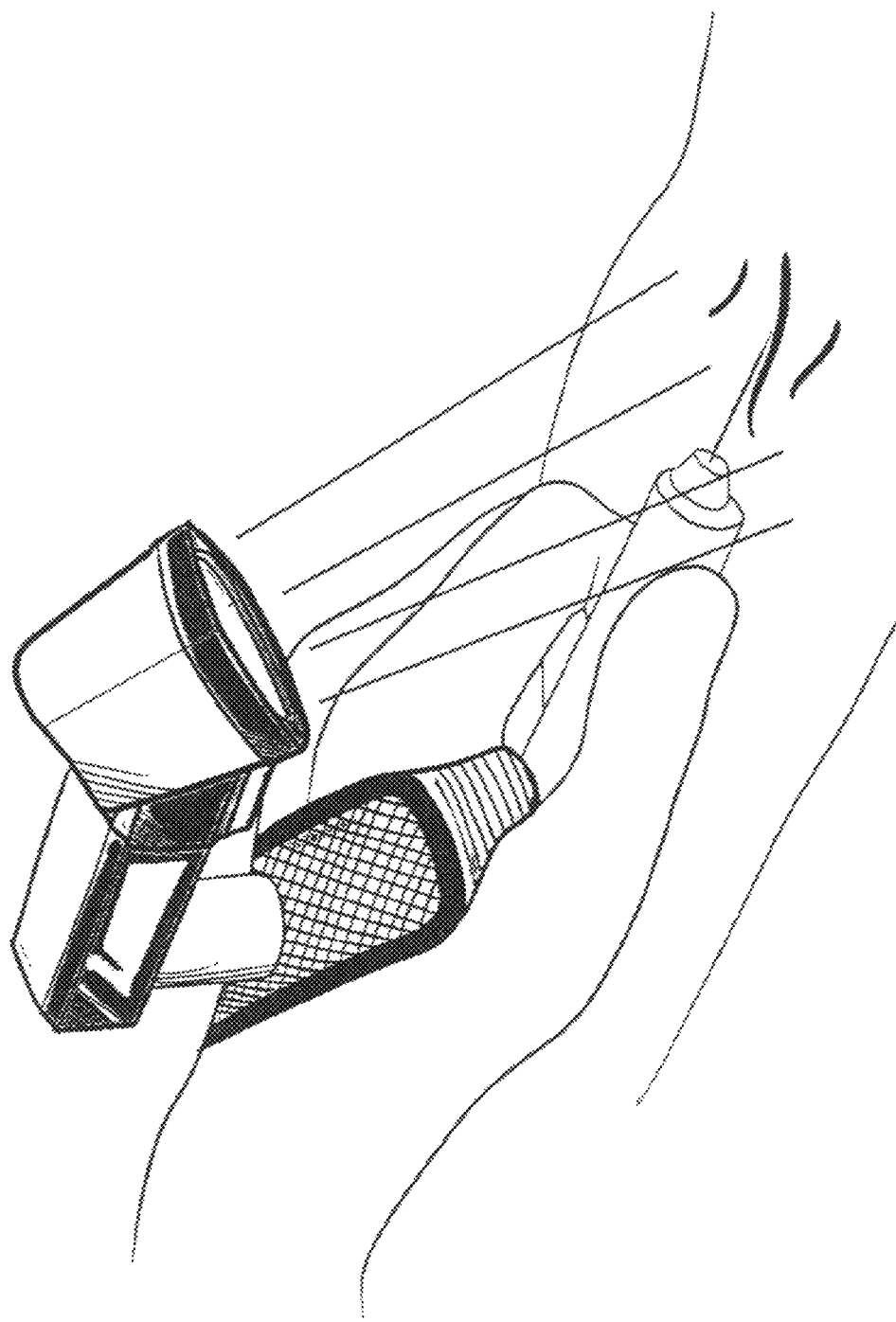

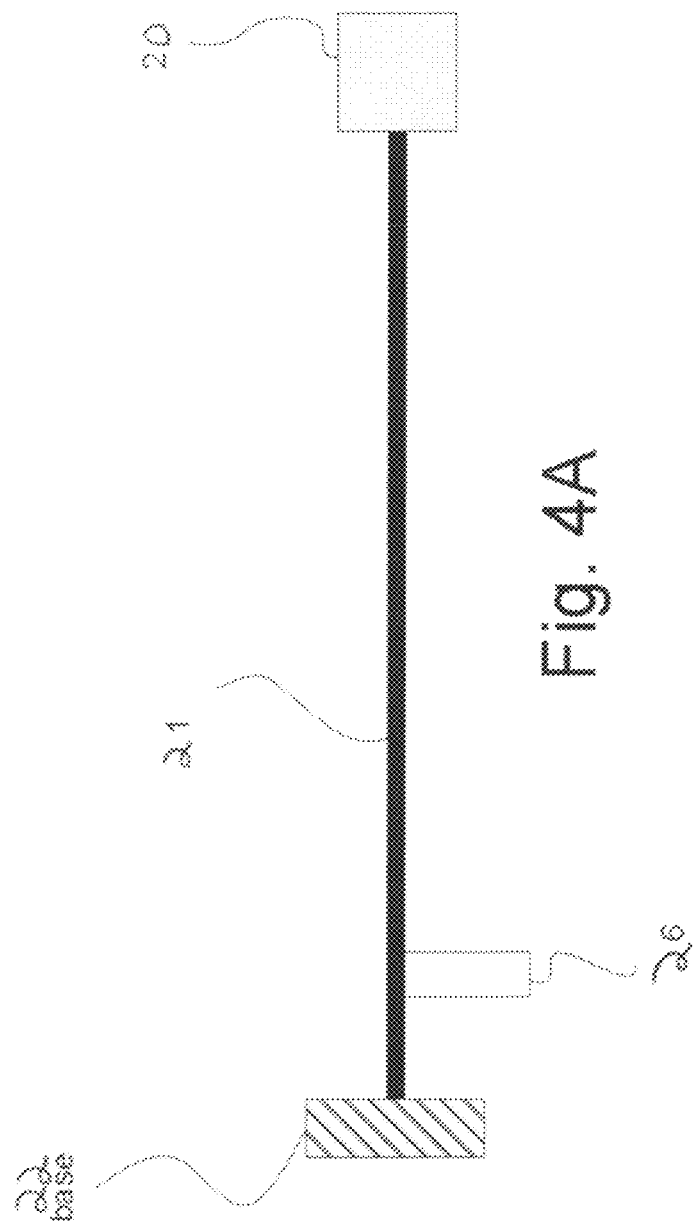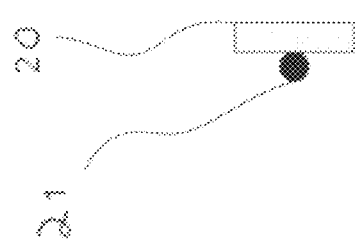

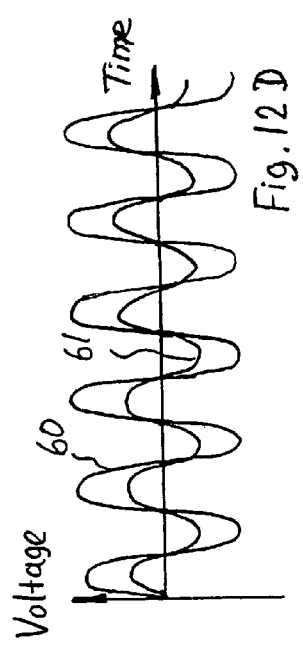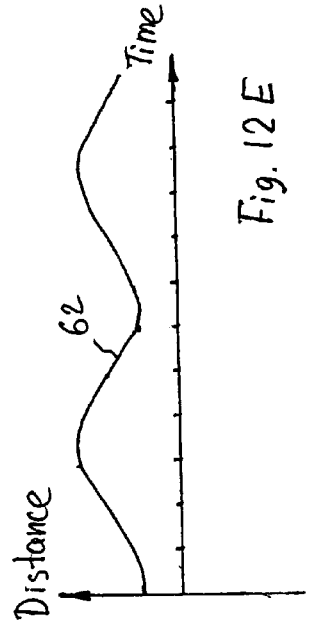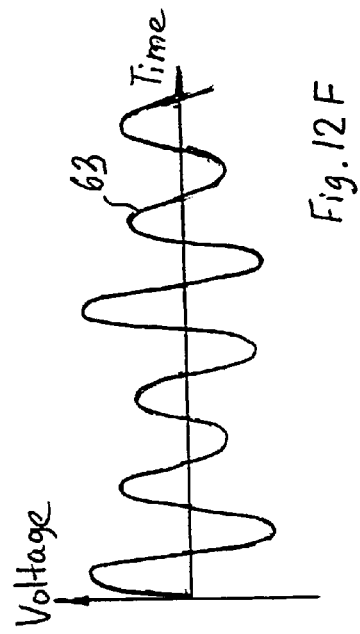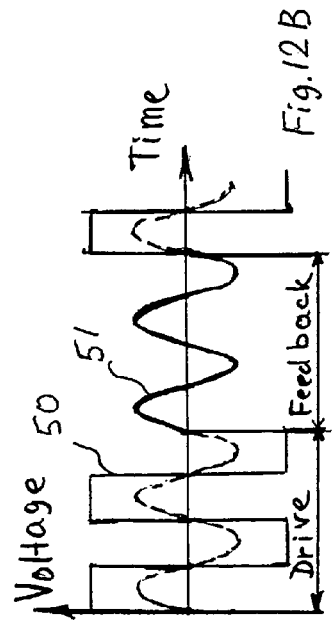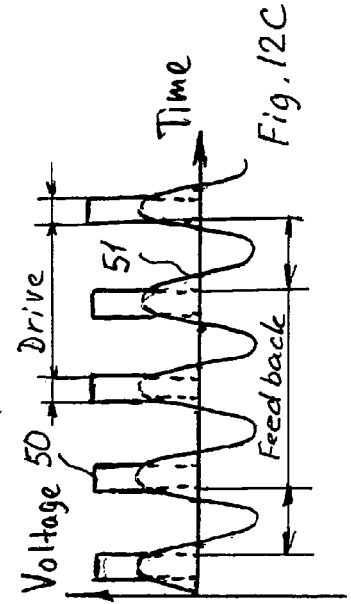

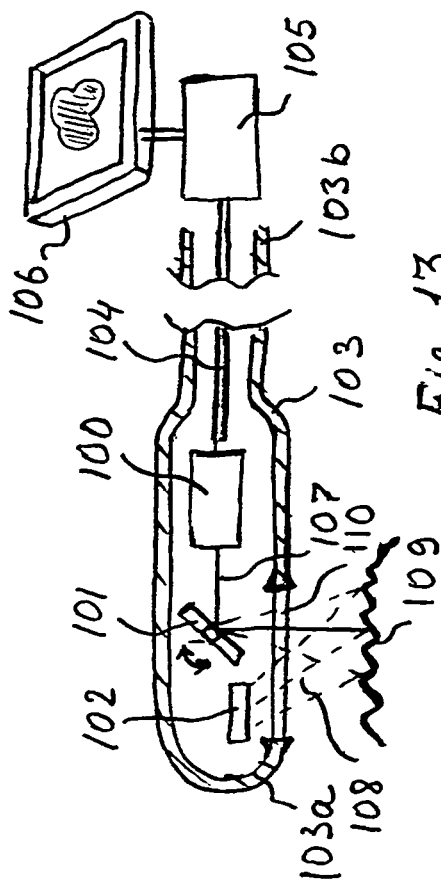
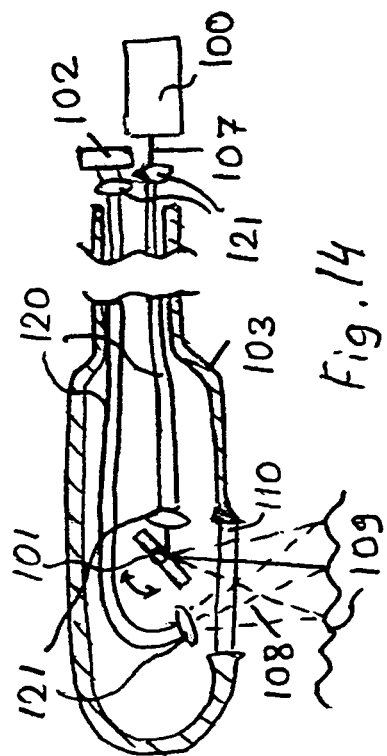
Fig. 13
Fig. 14

US 8,665,507 B2

MODULE MOUNTING MIRROR ENDOSCOPY

This application is a continuation in part of application Ser. No. 11/478,322, filed on Jun. 29, 2006, U.S. patent application Ser. No. 11/700,729, filed Jan. 31, 2007, and U.S. patent application Ser. No. 11/807,359, filed May 25, 2007. This application is also a continuation in part of U.S. patent application Ser. No. 12/215,713, filed Jun. 27, 2008, U.S. patent application Ser. No. 11/823,862, filed Jun. 28, 2007, and U.S. application Ser. No. 12/804,506, filed Jul. 22, 2010. This application claims priority on U.S. Application Ser. No. 61/279,980, filed Oct. 28, 2009. All the foregoing disclosures are hereby incorporated by reference.

FIELD OF THE INVENTION

The present invention is directed to the field of vein illumination on a patient. The invention is also direct to an apparatus for performing an endoscopy in medical procedures

BACKGROUND OF THE INVENTION

Vein illumination devices are known in the art. The vein illumination devices can have various mounting arrangements, including but not limited to mounting on a needle, on a head piece, on a tourniquet, on the back of the hand, and on a goose neck stand, etc. Various such devices are shown in our prior patent applications including of application Ser. No. 11/478,322, filed on Jun. 29, 2006, U.S. patent application Ser. No. 11/700,729 filed Jan. 31, 2007 and U.S. patent application Ser. No. 11/807,359 filed May 25, 2007, U.S. patent application Ser. No. 12/215,713 filed Jun. 27, 2008 and U.S. patent application Ser. No. 11/823,862 filed Jun. 28, 2007 and U.S. application Ser. No. 12/804,506 filed Jul. 22, 2010.

SUMMARY OF THE INVENTION

In one embodiment, the present invention is directed to a two-dimensional scanning arrangement for a laser vein-illumination device. The device includes a base and a frame connected to the base using at least one flexible hinge. The hinge allows the frame to move angularly with respect to the base in at least a first direction. The invention further includes a means for exciting angular oscillations of the frame at or near said frame's resonant frequency. An elastic torsional element having a proximal end rigidly attached to said frame and a distal end rigidly attached to a mirror is also included. The torsional element allows the mirror to move angularly with respect to the frame in a second direction, generally perpendicular to the first direction. There may also be a means for exciting the angular oscillations of the mirror.

The present invention also includes an imaging system. In one embodiment the device is for optically inspecting confined spaces having one or more small access orifices. The device includes at least one laser light source and a scanning means which scans one or more laser beam in a two-dimensional pattern over an inspection area. Also present is at least one light detector, sensitive to the light of the laser beam(s) being reflected from the inspection area. There is also a connecting member being thin and long enough to reach the inspection area through the access orifice. The device of the present invention has a variety of uses including but not limited to use as an endoscope in certain medical procedures.

BRIEF DESCRIPTION OF THE DRAWINGS

FIG. 1 shows each of the embodiments of FIGS. 1A to 3E in a single compilation demonstrating the general relationship between them.

FIG. 3D shows the back of the hand adaptor with a mechanical connector arranged to receive the head portion.

FIGS. 4A and 4B show an arrangement for moving a scanning mirror along a first axis.

FIG. 12B shows a graph of the feedback voltage in the drive and feedback state.

FIG. 12C shows a graph of the feedback voltage in the drive and feedback state where the drive and the feedback state are shorter than in FIG. 12B FIG. 12D shows a graph of the feedback voltage that is induced in the coil by the magnet.

FIG. 12E shows the distance between the coil and magnet that changes over time.

FIG. 12F shows the feedback voltage as a function of the distance between the coil and the magnet.

FIG. 13 shows an example of the endoscopic device of the present invention.

FIG. 14 shows an embodiment where one or more of the elements of the laser camera are moved from the distal end of the endoscope.

DETAILED DESCRIPTION OF THE INVENTION

Figure 1A:
FIG. 1A shows the removable head portion of the device of the present invention.
Figure 2:
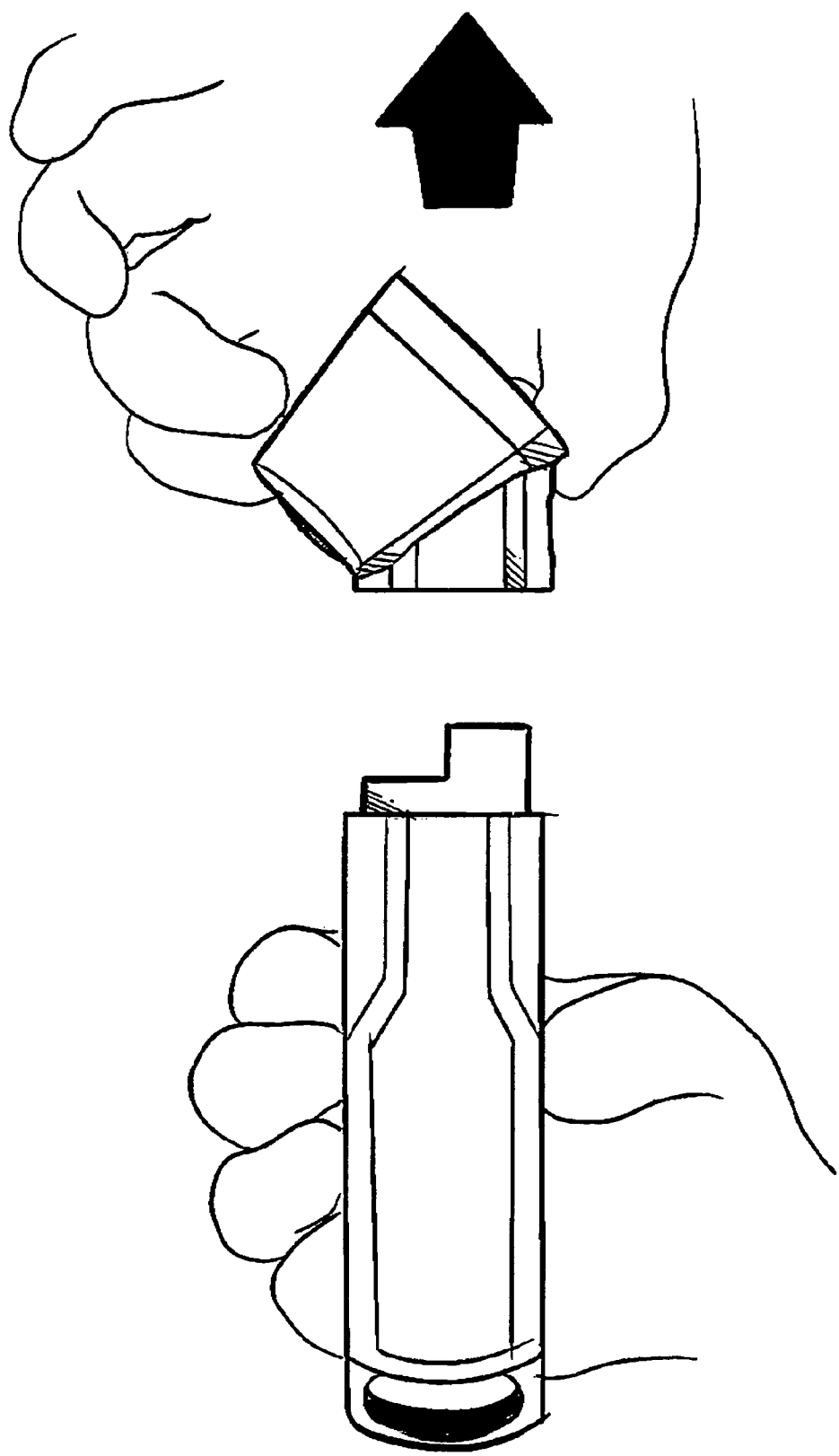
FIG. 2 shows how the head piece and body can be separated.

As seen in FIGS. 1-3 there is a laser based scanning device that includes a body 10 with a removable headpiece 11. The body and the head piece may be connected together by any suitable means. Preferably, there is an electrical connection between the body 10 and the headpiece. One or the other or both of the body and/or the headpiece may have a source of electrical power such as a battery.

FIGS. 1, 2 and 3A-3E show a modular design system wherein the device has a removable head portion that can be held (mounted) in a plurality of ways. FIG. 1 shows each of the FIGS. 1A-3E in a single compilation showing a relationship between them.

FIG. 2 shows a head portion on the right hand side of the drawing and a body portion of the left hand side. The head portion is a vein illumination device as previously described, including a small rechargeable battery for operating the unit for a short period of time. The body portion contains a larger battery, which is capable of charging the small battery when the two pieces are mated.

FIG. 1A shows the body portion and the head portion mated together and utilized in a handheld mode. While in this mated configuration, the unit can be placed in a charger (not shown) for charging the battery in the body portion and the smaller battery in the head portion. Alternatively, the charger can charge just the battery in the body portion, which in turn charges the smaller battery in the head portion. Still further, the charger can be arranged to receive just the body portion, and/or just the head portion, without them being mated, and charge their respective batteries.

FIG. 2 shows the head portion removed from the body portion. The mating provides electrical connections (for providing charging power from the body to the head) as well as mechanical connection between the two. When the head is removed it continues to run off its small battery and functions as a vein illumination device. The head can now be mounted on a plurality of types of devices (FIGS. 03A-03E), provided each device has a mechanical connector adapted to receive the mechanical connector of the head. Further, each of the plurality of types of devices could also contain a battery or power source which connects through the electrical connector and powers the head or charges the small battery in the head.

Figure 3A:
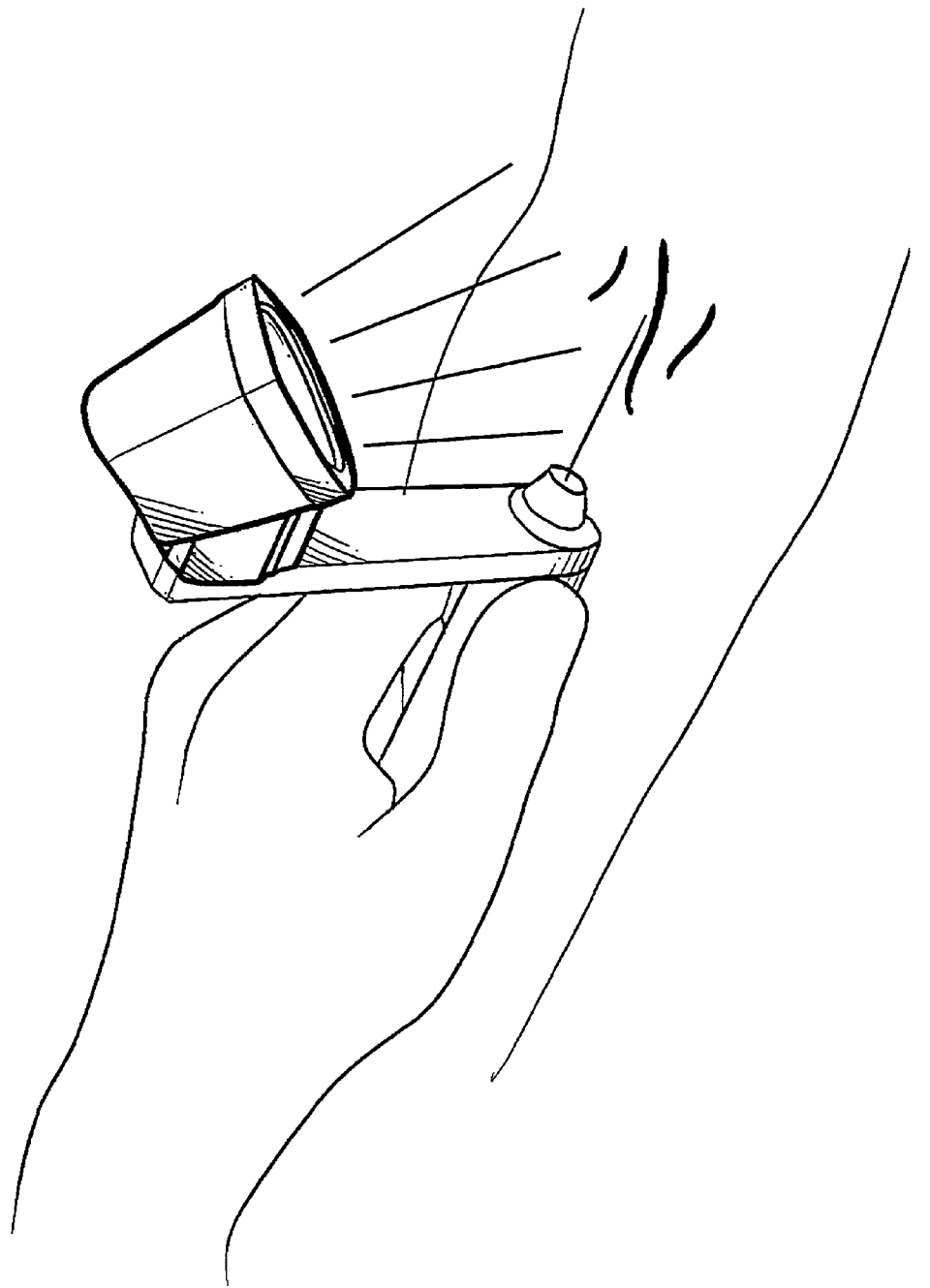
FIG. 3A shows the head piece mounted on a syringe.

FIG. 3A shows the head mounted on a syringe. The syringe has a mechanical connector arranged to receive the head. Alternative to a syringe, any device that is used for access to a vein can be arranged with a mechanical connector to receive the head. For example, but not limited to, a vacutainer, iv kit, butterfly, hypodermic, etc.

Figure 3B:
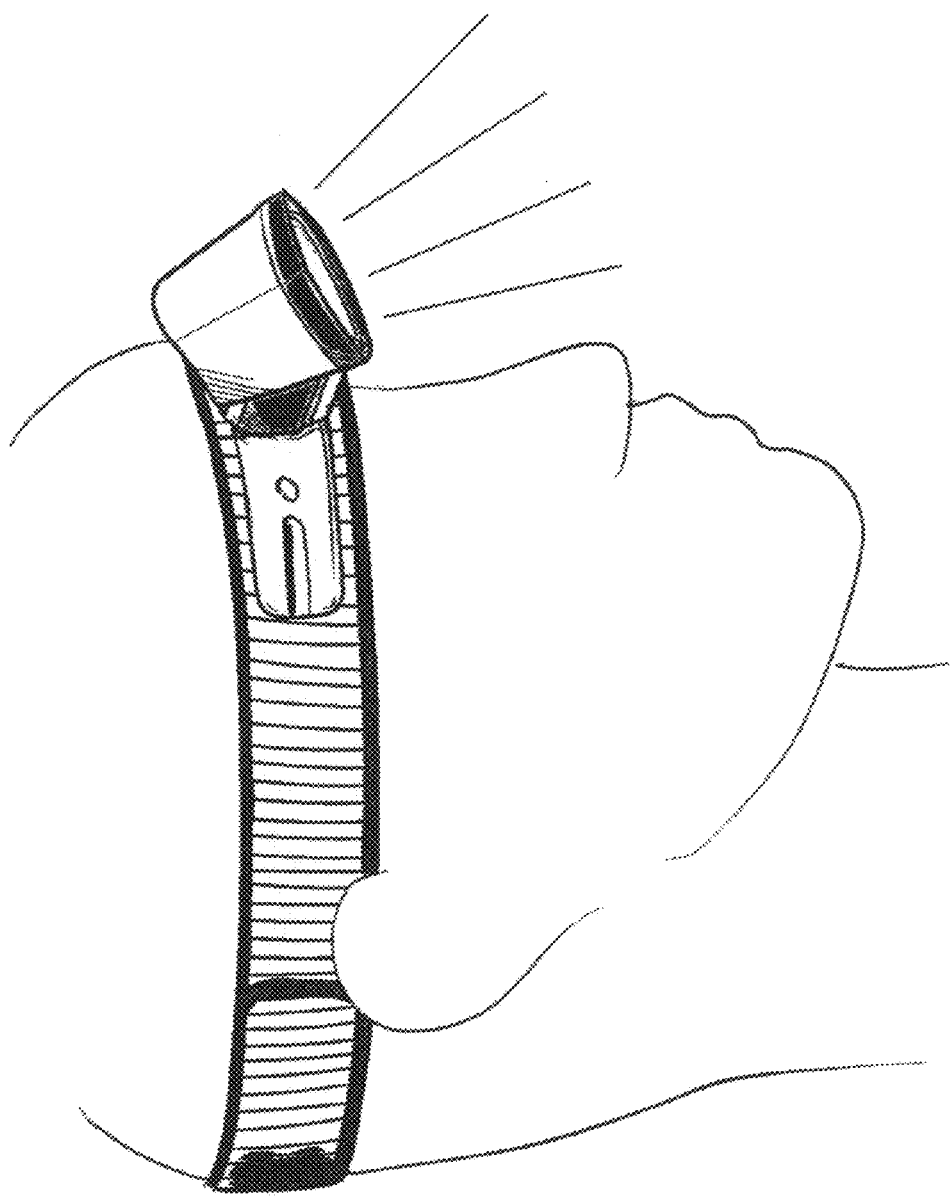
FIG. 3B shows a head piece with a mechanical connector arranged to receive the head portion of the device.

FIG. 3B shows a head piece with a mechanical connector arranged to receive the head portion of the device. The head piece is shown as a band, however, any device mounted to the head or body can be arranged with a mechanical connector for receiving the head piece of the device. For example, but not limited to, a hat, helmet, miners hat, fireman's hat, surgeon's hat, eye glasses, etc.

Figure 3C:
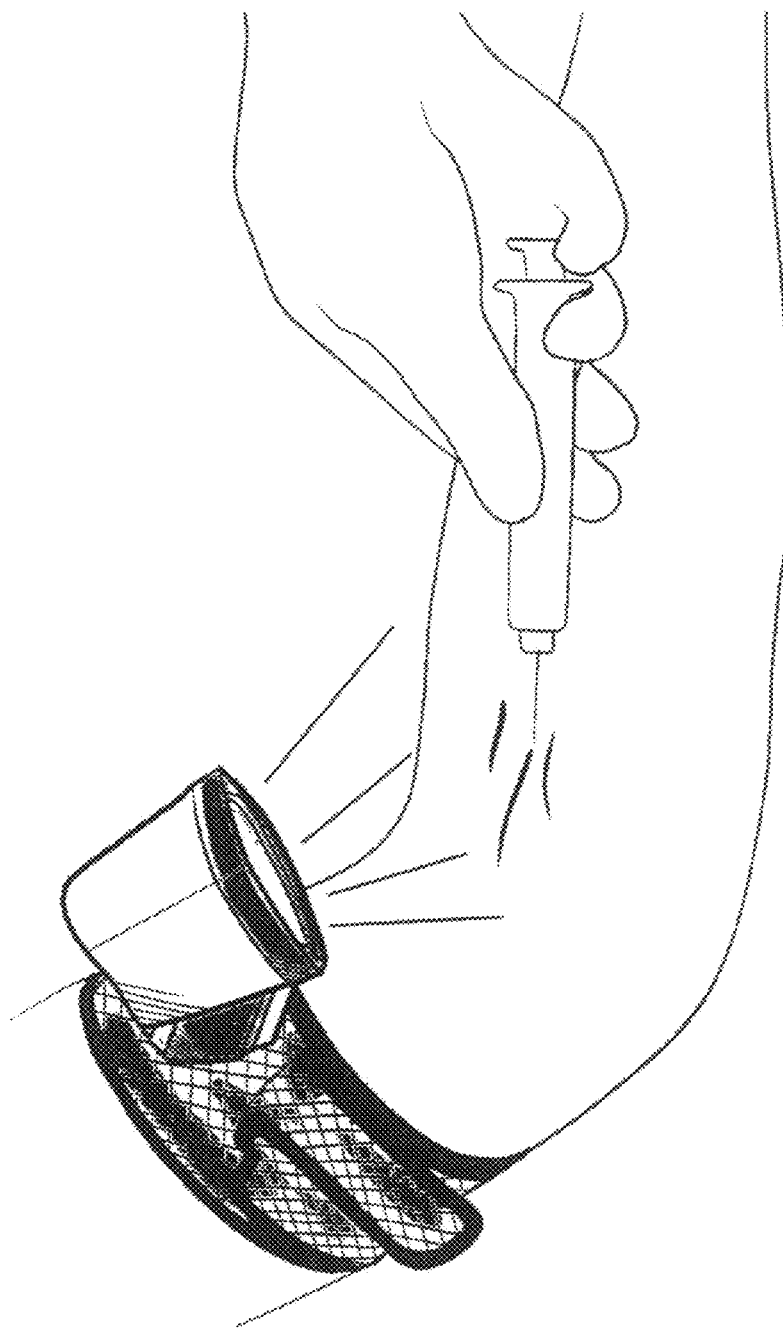
FIG. 3C shows a tourniquet piece with a mechanical connector arranged to receive the head portion of the device.

FIG. 3C shows a tourniquet piece with a mechanical connector arranged to receive the head portion of the device. The tourniquet can be a manual type or can be a pump driven device.

FIG. 3D shows a back of the hand adaptor with a mechanical connector arranged to receive the head portion of the device. The back of the hand adaptor can be a strap that attaches around the hand, or alternatively, can be a glove or other connection device. Further, the adaptor can attach to the fingers, such as, for example, a connection configured as brass knuckles, or a ring, or a ring that covers more than one finger.

Figure 3E:
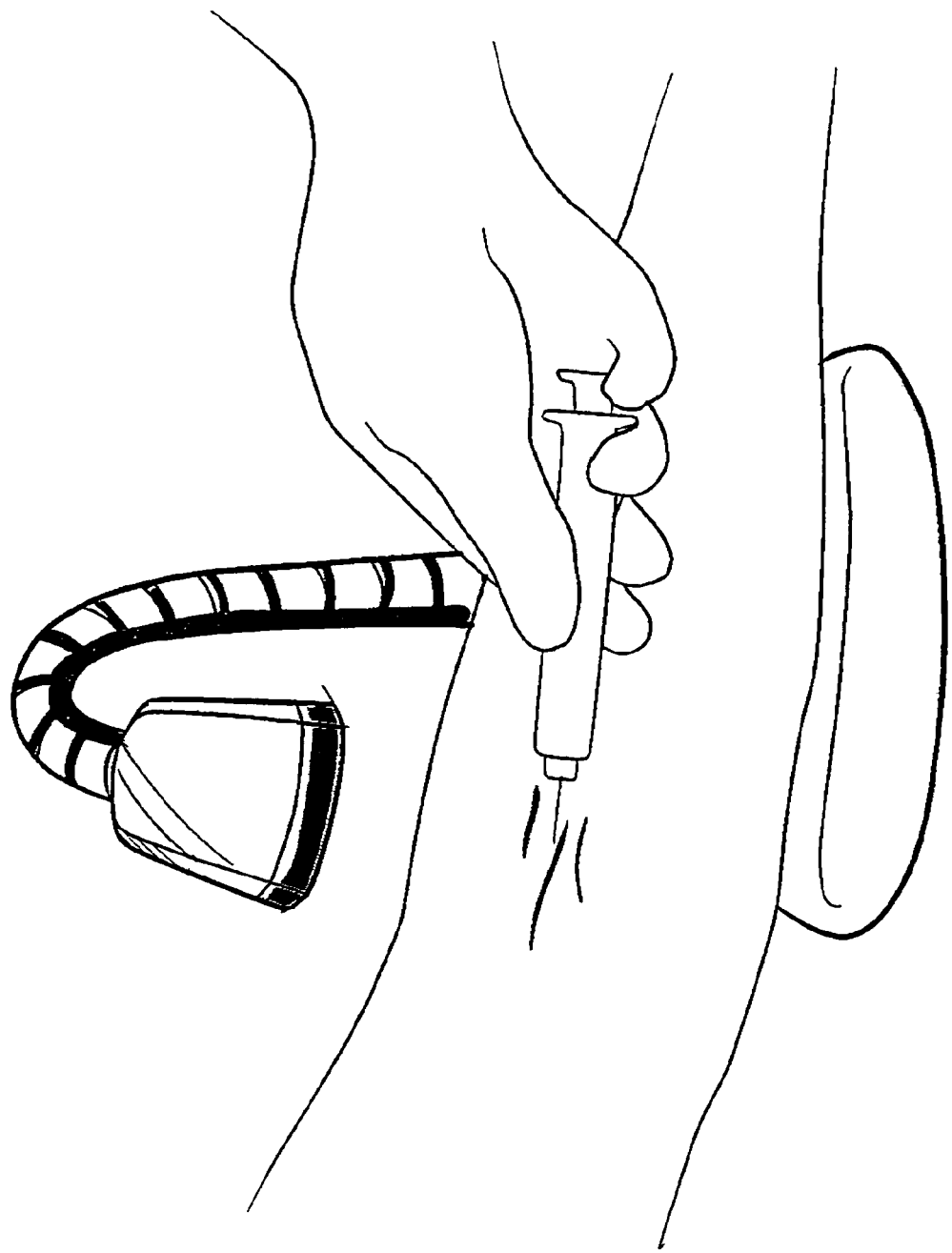
FIG. 3E shows a flexible arm with a mechanical connector arranged to receive the head portion of the device.

FIG. 3E shows a flexible arm with a mechanical connector arranged to receive the head portion of the device. The flexible arm can be configured to mount in a variety of ways, such as, but not limited to, clamping, having a weighted base, fasteners, connected to rolling wheels, etc.

Figure 5:
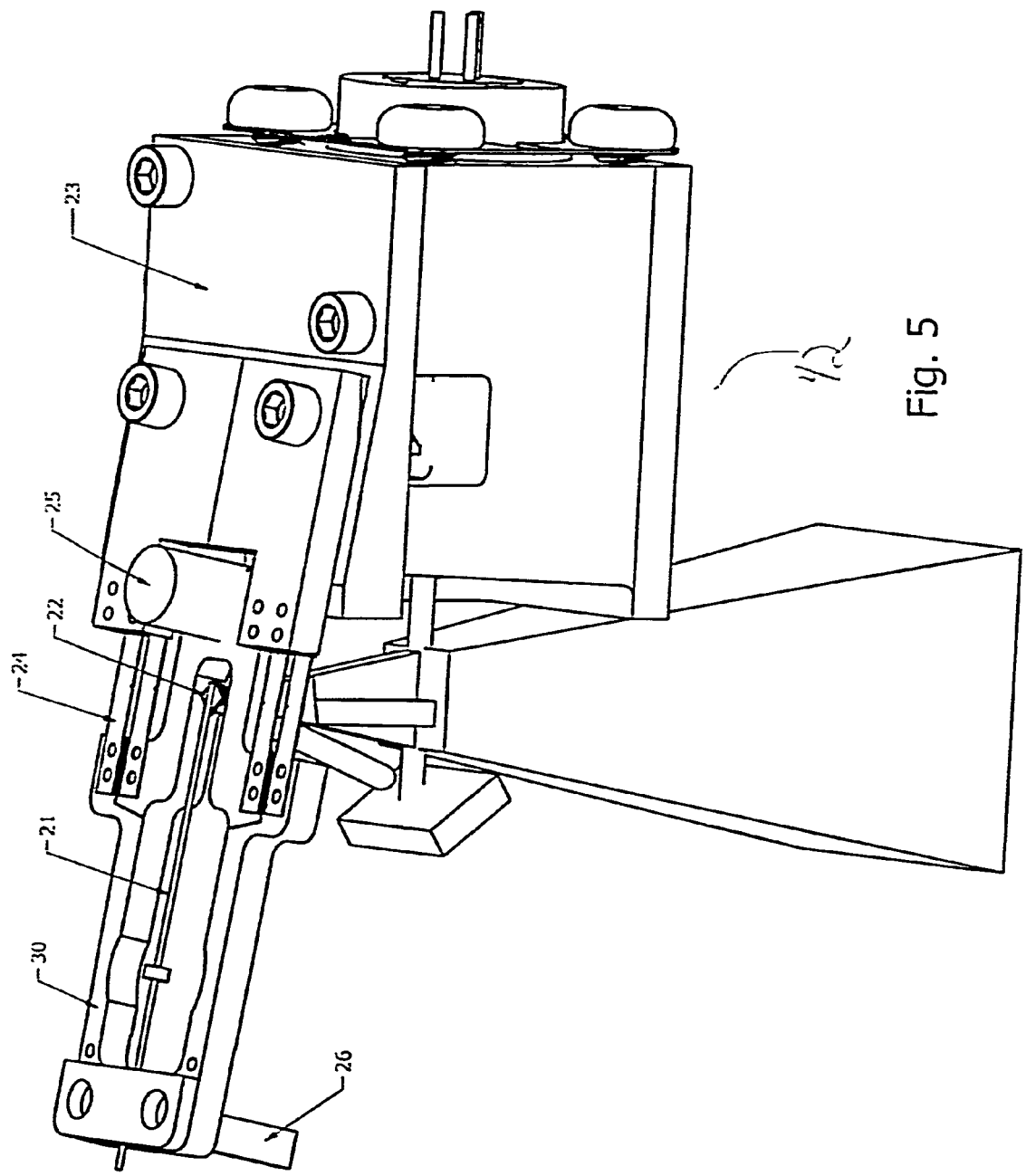
FIG. 5 shows the elements of FIGS. 4A and B mounted on a frame.
Figure 6:
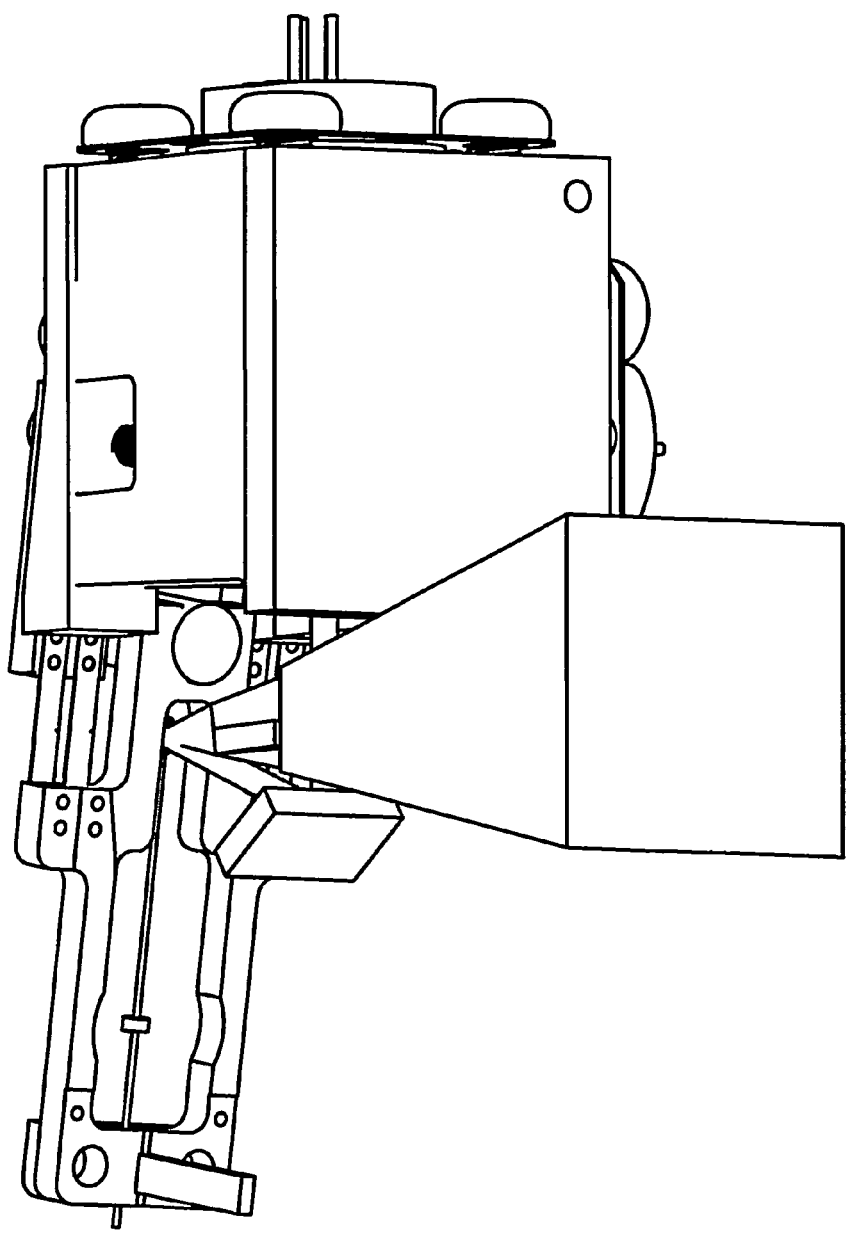
FIG. 6 shows a bottom perspective view of the device of FIG. 5.
Figure 7:
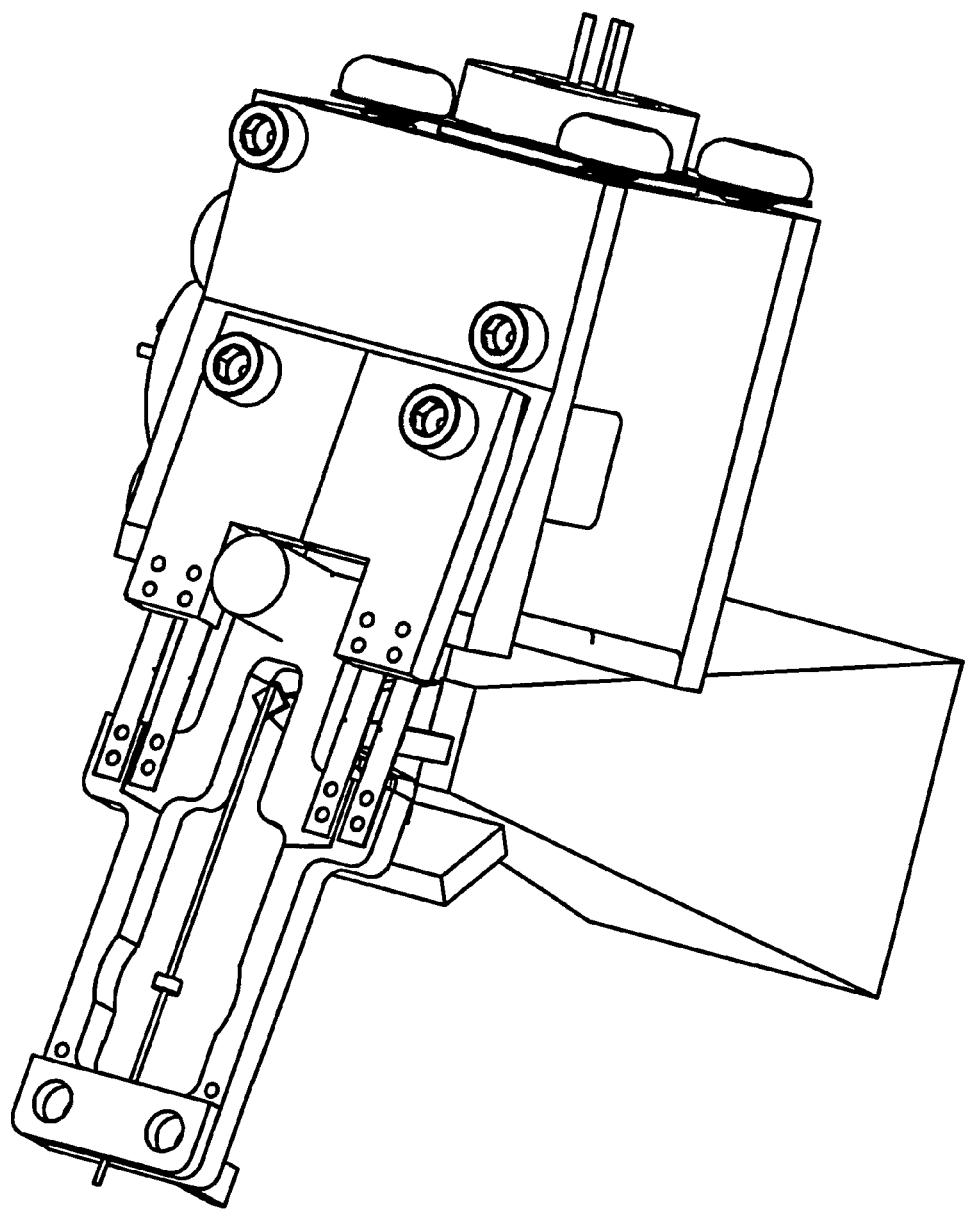
FIG. 7 shows a top rear perspective view of the device of FIG. 5.
Figure 8:
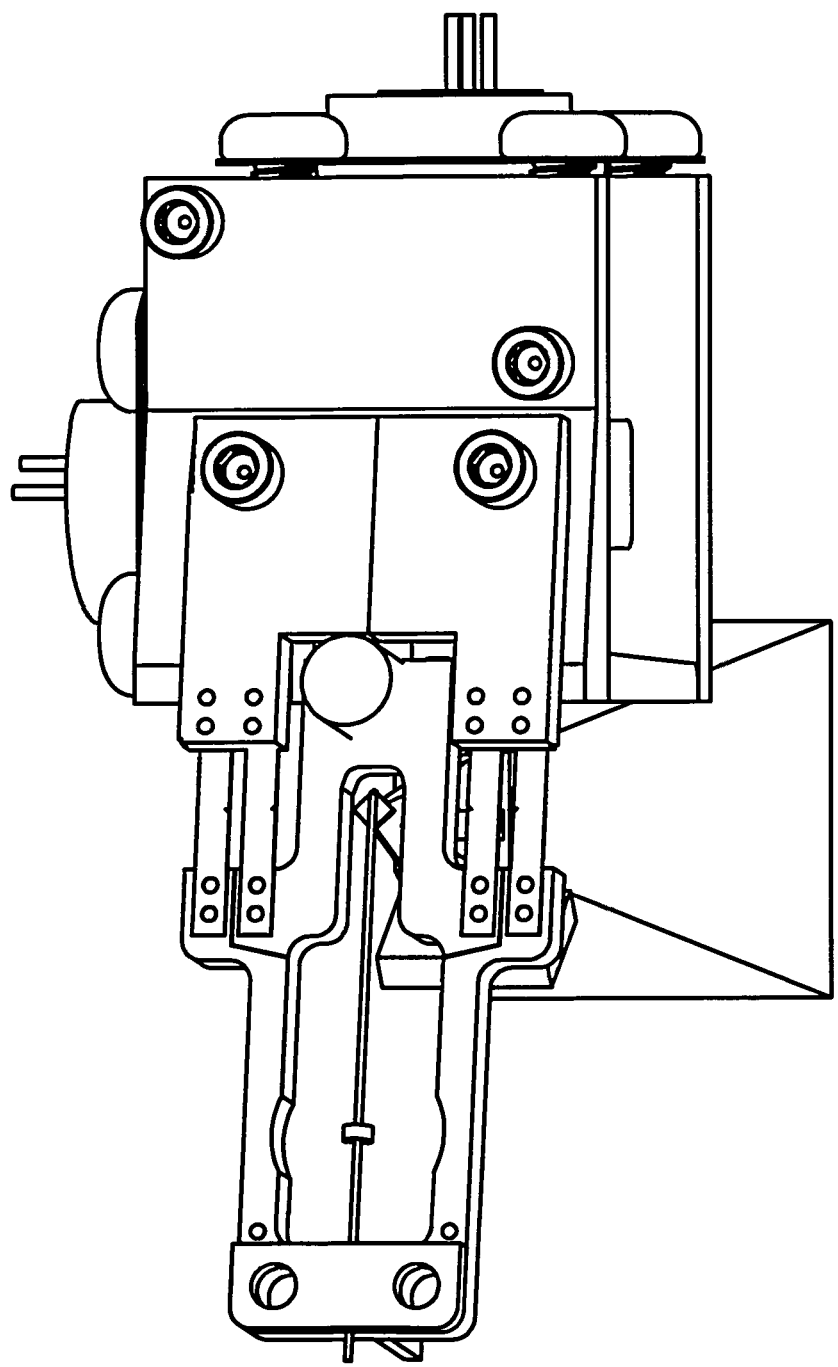
FIG. 8 shows a center perspective view of the device of FIG. 5.
Figure 9:
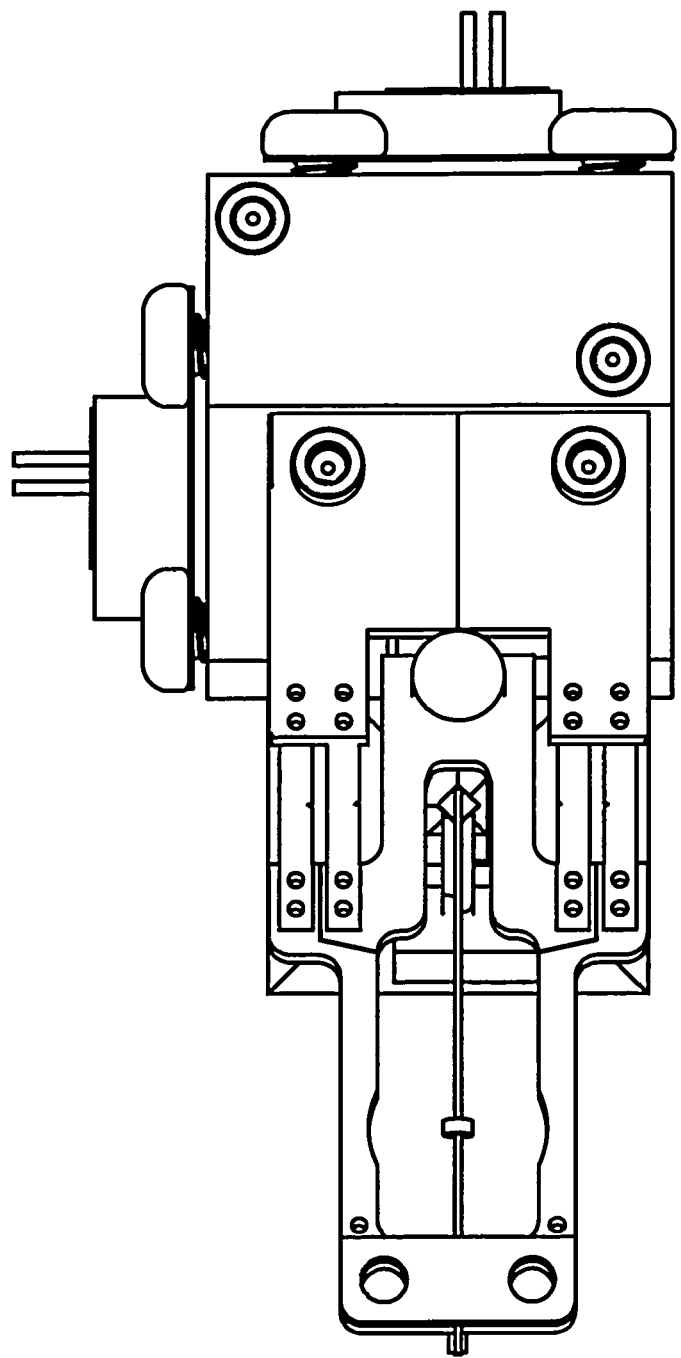
FIG. 9 shows a top view of the device of FIG. 5.
Figure 10:
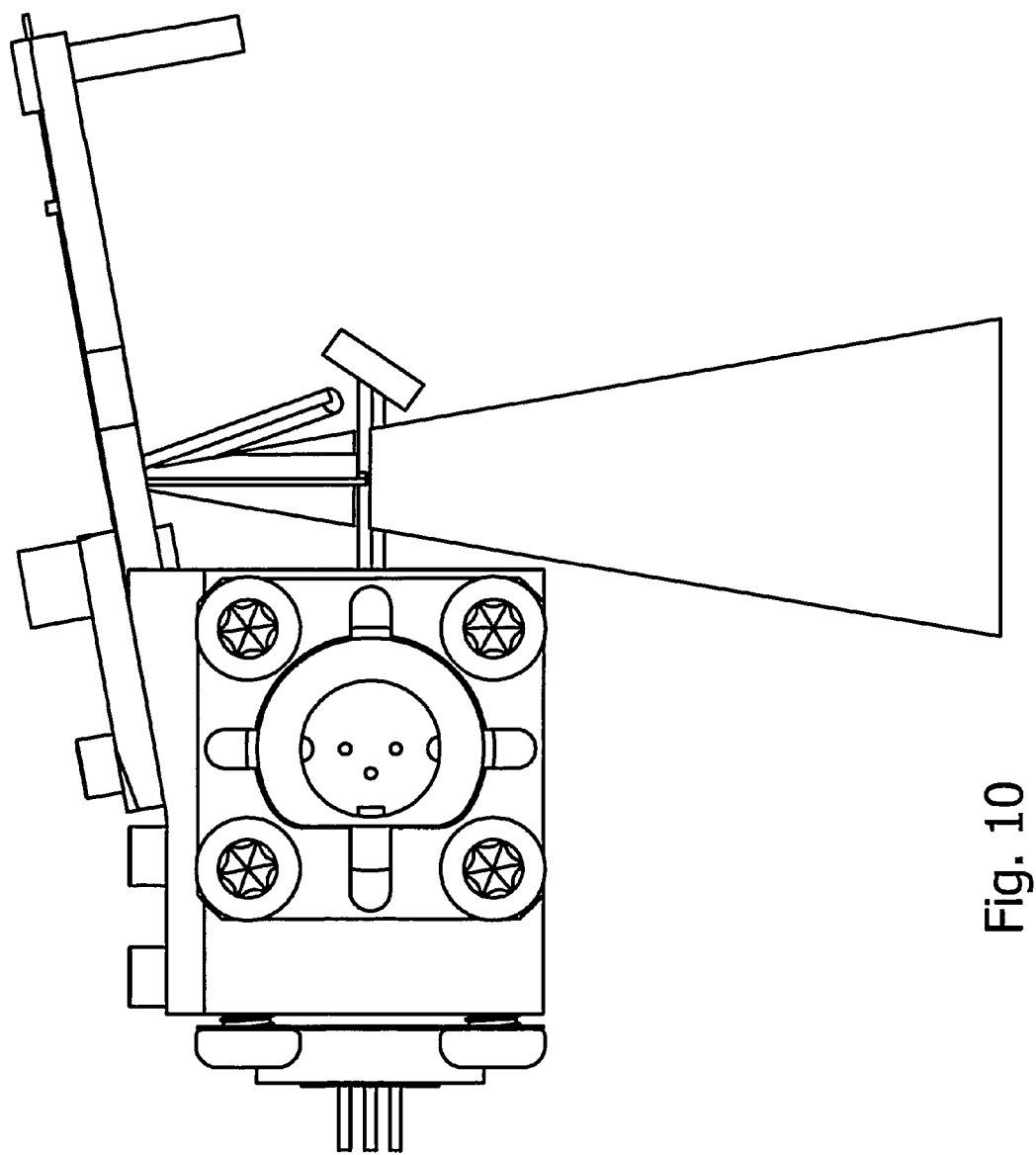
FIG. 10 shows a side view of the device of FIG. 5.
Figure 11:
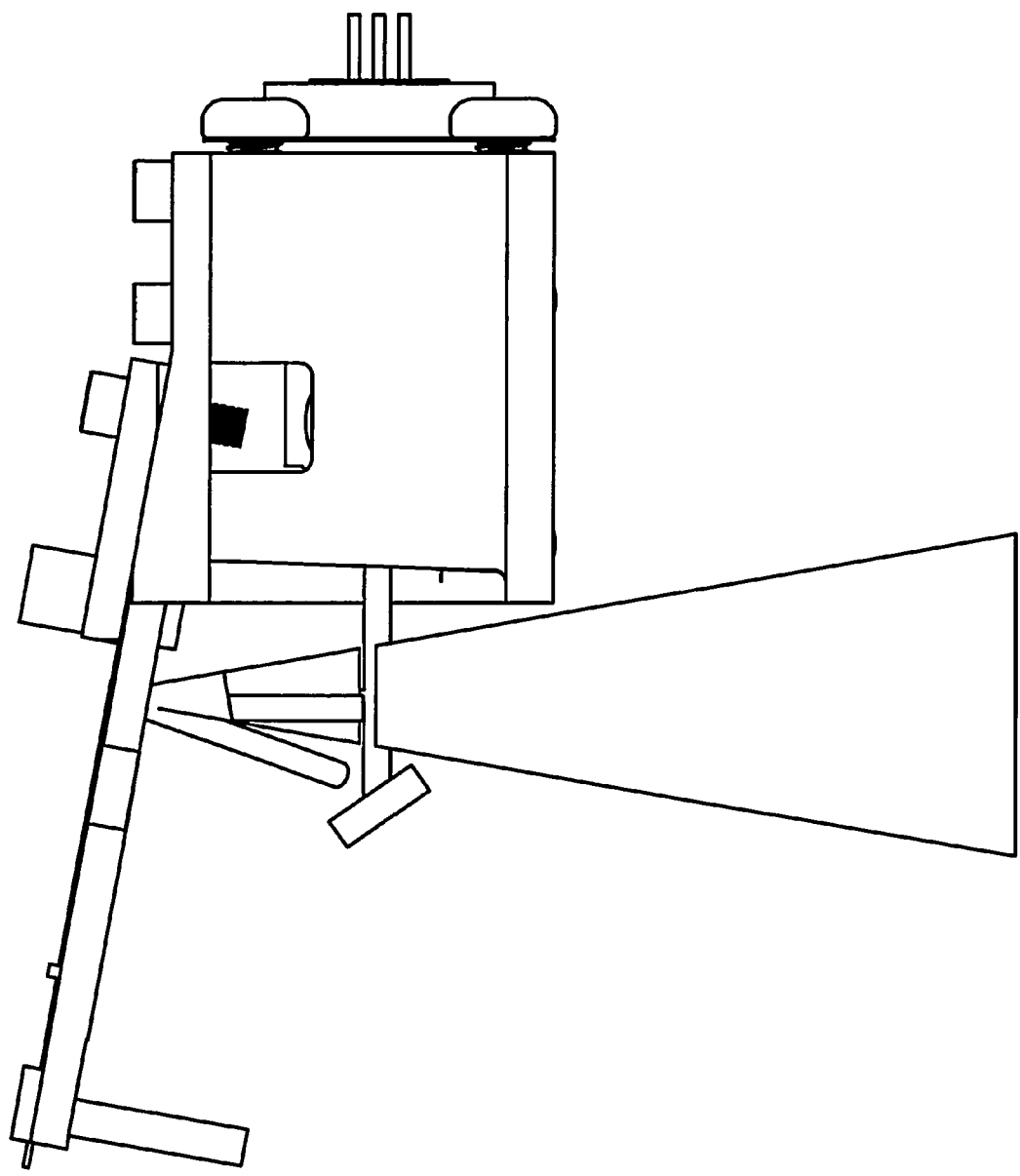
FIG. 11 shows a side view of the opposite side of the device of FIG. 5.

In FIGS. 4A, 4B and 5, an arrangement for moving a scanning mirror along two perpendicular axes is described. FIGS. 4A and 4B show the mechanics for moving the mirror 20 along a first axis. A glass fiber 21 with a small diameter, for example diameter in the range of about 0.05 mm to about 0.5 mm may be used. In one embodiment the diameter may be about 0.21 mm. The fiber extends from a base or holder 22 to a mirror 20. The length of the fiber is preferably from about 5 mm to about 50 mm. The mirror can vary in size as well. In this embodiment, the length of the fiber is about 11 mm and the dimension of the mirror is about 0.9 mm by 9 mm. It will be appreciated by those skilled in the art that other lengths or dimensions can be used. The mirror is secured onto the fiber 21 by for example glue or other suitable connecting material. A piezo-electric element 26 is then secured with one end attached to the fiber 21 and the other end floating. Glue, for example, may be used to secure the piezo-electric element to the fiber. Alternatively, the piezo-electric element 26 can be attached to a common base to which the fiber 21 is attached as well, and vibrations are still passed to the fiber 21. When the piezo-electric element 26 is excited with the electrical signal of the frequency equal to the frequency of the torsional resonance of the fiber-mirror system, which in this embodiment happens to be 18.5 kHz, it vibrates and induces the corresponding angular displacements to the attached fiber at the same rate of 18.5 kHz. Other fiber mirror systems may have a different torsional resonance frequency. Due to the high quality factor of the fiber-mirror system, the angular displacement of the mirror is many times greater than that of the opposite end of the fiber and in this embodiment reaches approximately ±7 degrees. The torsion node of the fiber may be higher than fundamental, meaning that at least one torsional node, i.e. a cross-section of the fiber which remains still during oscillations, is formed. Such nodes allow for generally higher oscillation frequency at the expense of generally lower oscillation amplitude.

It has been found that the amplitude of mirror rotation is dependent on the thickness and length of the fiber, the size and weight of the mirror, and the frequency and intensity at which the piezo-electric element shakes the fiber 21.

FIG. 5 shows the elements of FIG. 4A mounted in a frame 30. In this embodiment, the piezo-electric element 26 is mounted to the frame which in turn holds the end of the fiber 21 opposite to the mirror (acts as the base from FIG. 4A). The frame 30 connects by four rectangular brass hinges 24 to a base 23. Preferably, both ends of the hinges are soldered to the frame and to the base, so the frame can move angularly with respect to the base. In one embodiment the base 23 may have vein scanning device similar to the vein scanning device shown in copending U.S. application Ser. No. 12/804.506 filed Jul. 22, 2010.

Besides soldering other connection methods may be employed as well, such connection methods preferably allowing for both mechanical rigidity and electrical conductivity. In addition to providing mechanical support for the frame and acting as springs in a resonant system, the hinges may also serve as electrical conductors for drive and feedback signals. A magnet 25 is also attached to the frame 30. The geometry of the brass hinges are selected so that the resonant frequency of moving the frame 30 (and the attached mirror elements from FIG. 4A) is approximately equal to the desired frequency of the motion of the mirror 20 about the second axis perpendicular to the first axis. An electric coil (not shown) is used for creating the variable magnetic field around the magnet 25. In response, the magnet 25 generates the torque which in turn causes the frame to rotate about the second axis. For optimal efficiency, the coil should be placed as close as possible to the magnet, however, minimal mechanical clearance sufficient for the magnet to move without mechanical interference should be observed. It is particularly advantageous if the second axis passes through the center of the mirror 20, as in this case the center of the mirror experiences very little or no translational motion which facilitates aligning the mirror with the incoming laser beam. It has been found that there is little or no crosstalk between two axes of mirror oscillations in this arrangement.

Figure 12:
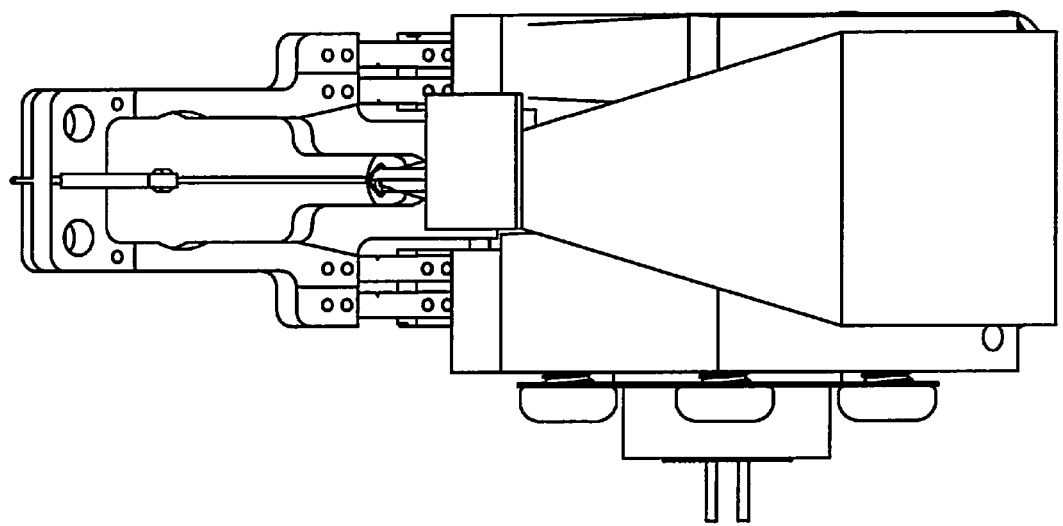
FIG. 12 shows a bottom view of the device of FIG. 5.
Figure 12A:
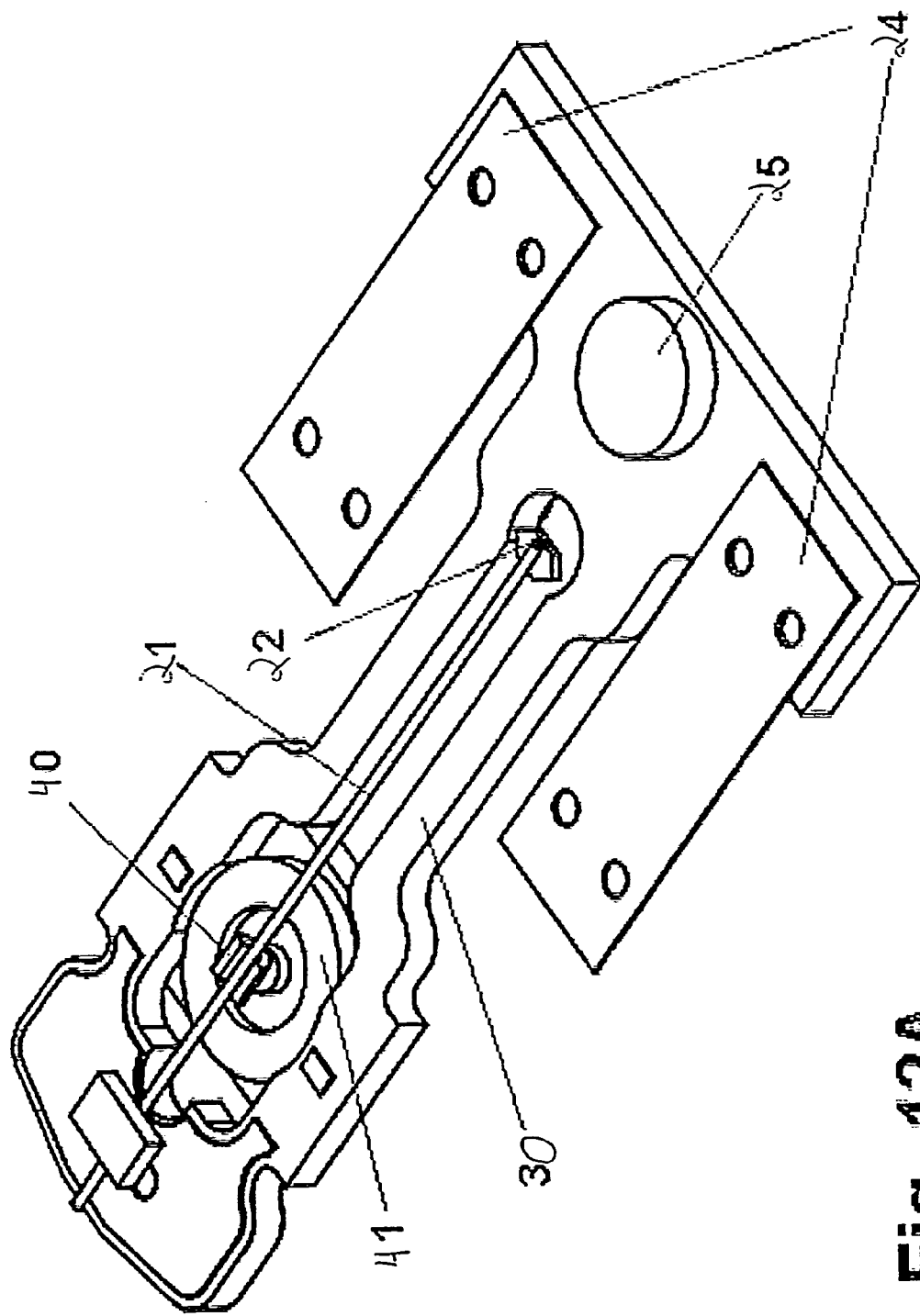
FIG. 12A shows a top view of the frame of the endoscope.

It may also be beneficial to attach another permanent magnet 40 to the fiber 21, so the coil 41 may be used to drive the oscillation of the mirror 20 in the first direction (around the axis of the fiber), as illustrated by FIG. 12A. Likewise, these coil and magnet should be as close as possible to each other with only a necessary clearance left between them. The same magnet-coil pair can be used to collect positional feedback from the mirror. Furthermore, the coil may be switched between drive state and feedback state in time, as illustrated on FIG. 12B. As the magnet attached to a fiber or a frame engages in oscillations, the feedback voltage 51 is induced in the coil. During feedback state, no external voltage is applied to the coil, so the feedback voltage 51 may be amplified, digitized or otherwise processed by electronic control circuits (not shown). During drive state, the external voltage 50 is applied to the coil, thus providing power for sustained mechanical oscillations. Alternatively, the drive and feedback states may be shorter, occupying only a portion of an oscillation cycle as shown on FIG. 12C. Variable and non-periodic switching between drive and feedback states are possible as well.

Additionally, since in the process of oscillation in the second direction (frame 30 oscillation) the distance between magnet 40 and coil 41 changes, the amplitude of the feedback signal from mirror oscillation will be changing depending on the position of the frame, thus enabling frame positional feedback collection from the same magnet-coil pair. FIG. 12D shows, as a function of time, a comparatively large feedback voltage 60 induced in the coil while the magnet is in its closest position to the coil, and a comparatively small feedback voltage 61 induced in the coil while the magnet is in its furthest position from the coil, FIG. 12E shows the distance 62 between the coil and the magnet, changing due to frame oscillations. Finally, FIG. 12F shows the resulting feedback voltage 63. Largest amplitude of this voltage corresponds to the closest proximity between the coil 41 and the magnet 40 FIGS. 6-12 show various views of the device of FIG. 5.

A laser camera 42 can be used at the end of an endoscope to form a laser-based endoscopic imager. These applications include but are not limited to U.S. patent application Ser. No. 12/215,713, filed Jun. 27, 2008, U.S. patent application Ser. No. 11/807,064 filed May 25, 2007 and U.S. patent application Ser. No. 11/807,359 filed May 25, 2007 the disclosures of which are incorporated herein by reference. Generally, unlike a conventional CCD (Charge-Coupled Device) or CMOS (Complementary Metal-Oxide-Semiconductor) camera, which uses defused illumination and a large array of light-sensitive detectors, a laser camera uses a scanning laser beam as an illumination source and a single detector, which receives the laser light reflected from the surface of interest. In one possible arrangement, illustrated by FIG. 13, the main elements of a laser camera, such as a laser light source 100, a scanning arrangement 101 and a light detector 102 are all located at a distal end 103a of a thin connecting member 103, which serves to bring the endoscope to a close proximity with the area to be inspected. The laser beam 107 is formed into a raster by the scanning arrangement 101 and directed toward the inspection area 109 through an optical window 110. The reflected light 108 reaches the light detector 102, carrying the information about the inspected area.

Connecting member 103 may be flexible, as well as rigid. As typical for endoscopy applications, said inspected area is usually situated in a confined space with only a small access orifice available, hence maintaining the minimal thickness of the endoscope is essential. Such confine spaces include the inner cavities of human body, other biological objects, as well as manufactured objects, such as pipelines or engine cylinders. Referring further to FIG. 13, the proximal end 103b of the connecting member does not go into confined spaces and hence does not need to be miniaturized. The proximal end carries the control block 105, responsible for power supplies, signal processing, user interface and other auxiliary functions, and an LCD screen 106 or other means of visually presenting the optical information gathered from the inspected area to the eyes of the User. In this embodiment, said optical information is delivered from the distal end of the endoscope electronically, through cable bundle 104, which runs the length of the endoscope. In other arrangements, said cable bundle may also include optical fibers or any combination of electronic and optical signal delivery means.

For the purpose of keeping the endoscope as thin as possible, it may be advantageous to move some or all of the elements of the laser camera from the distal end of the endoscope to its proximal end. An arrangement which exemplifies this idea is presented on FIG. 14. Here, the laser light source 100 and a light detector 102 are at the proximal end. Optical fibers 120 are delivering laser light to the scanner 101, which is still at the distal end. The reflected light 108, carrying the information about inspected area, is also delivered to the light detector through optical fibers. Additional optical elements 121, such as lenses, might be needed to efficiently couple the light into and out of the optical fibers.

Figure 15:
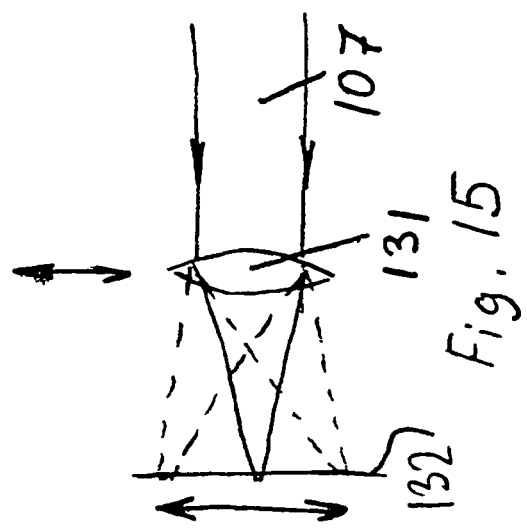
FIG. 15 shows a scanning arrangement where the lens linearly oscillates in a direction perpendicular to the laser beam.

Typically, the scanning arrangement 101 would include two angularly-oscillating mirrors or one bi-axial mirror. However, other scanning methods may be used as well. One of them is illustrated on FIG. 15, where the laser beam 107 is directed towards a lens 131, which linearly oscillates in the direction perpendicular to the laser beam. Assuming that the laser beam is collimated or nearly collimated, the lens would focus the beam into a focal plane 132, while scanning the focused spot along the direction of its own oscillations.

Figure 16:
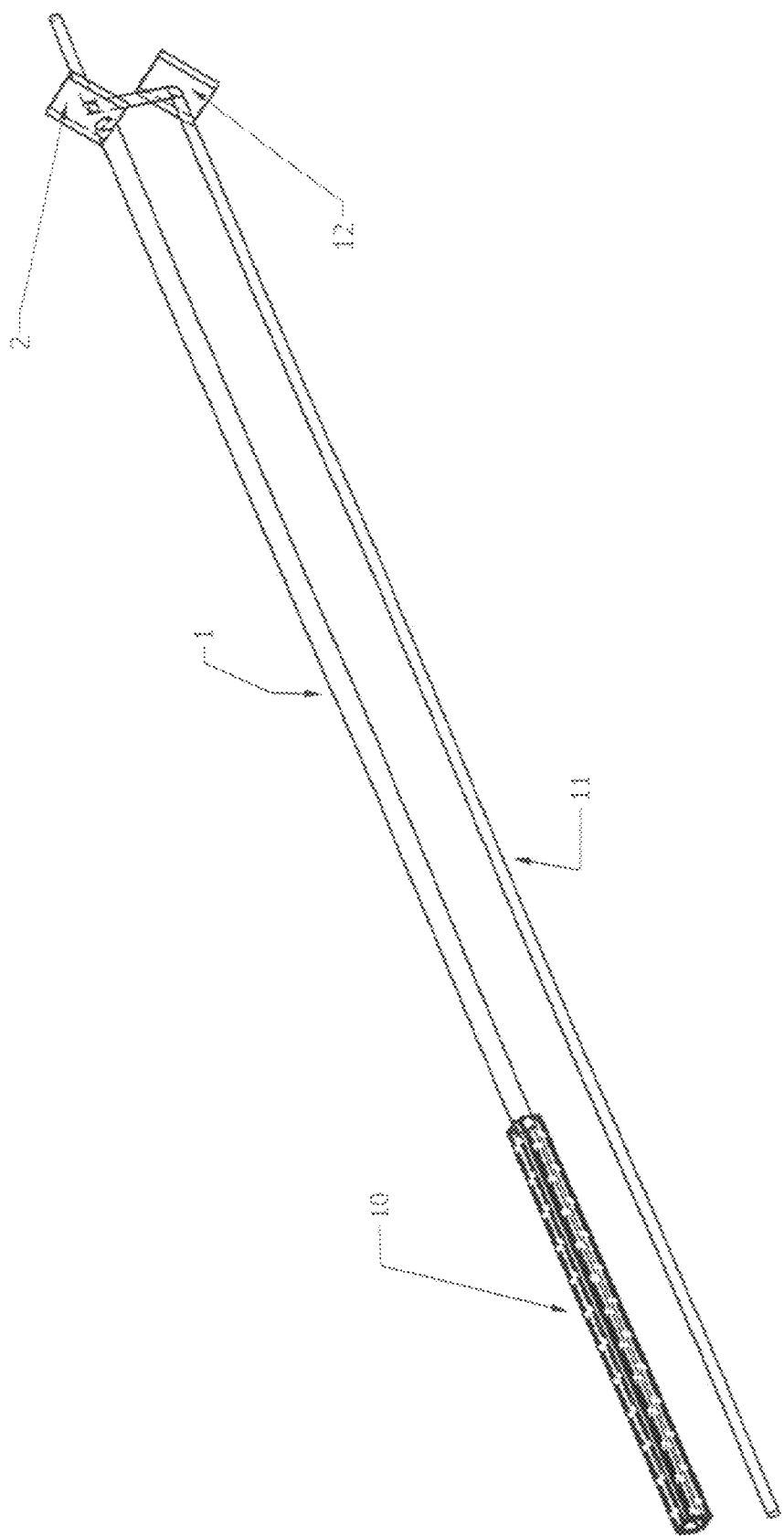
FIG. 16 shows an alternative embodiment of a scanning arrangement.

Another possible scanning arrangement is depicted on FIG. 16. A fiber 1 connects to a mirror 2 which is mounted at an angle (in this example 45 degrees) to the center lengthwise axis of the fiber 1. The mirror is mounted so that the center of mass of the mirror is not along the center lengthwise axis of the fiber 1. It should be noted that this fiber 1 is used as a mechanical structure and is not carrying any of the laser light. Four piezo-electric elements 10 are positioned in a rectangle around the base of the fiber 1. The piezo-electric elements 10 are affixed to the fiber 1 at the end closer to the mirror 2. The other end of the piezo-electric elements are affixed to the tubing of the endoscope (not shown). Two opposing piezo elements are driven at a high frequency (1 khz to 30 Khz) to cause the fiber to vibrate, which in turn results in the mirror rotating approximately about the center lengthwise axis of the fiber 1 in the manner previously described with reference to FIGS. 4A and 4B. The other two opposing piezo elements are driven at a lower frequency (60 hz-1000 hz) and cause the fiber 1 and therefore the attached mirror 2 to move about a second axis.

Still referring to FIG. 16, a laser light 11 is carried through a fiber cable in the endoscope (not shown) and is then reflected off a bounce mirror 12 (in this example 45 degrees) onto the moving mirror 2 which projects a raster pattern out the tip of the endoscope.

Figure 17:
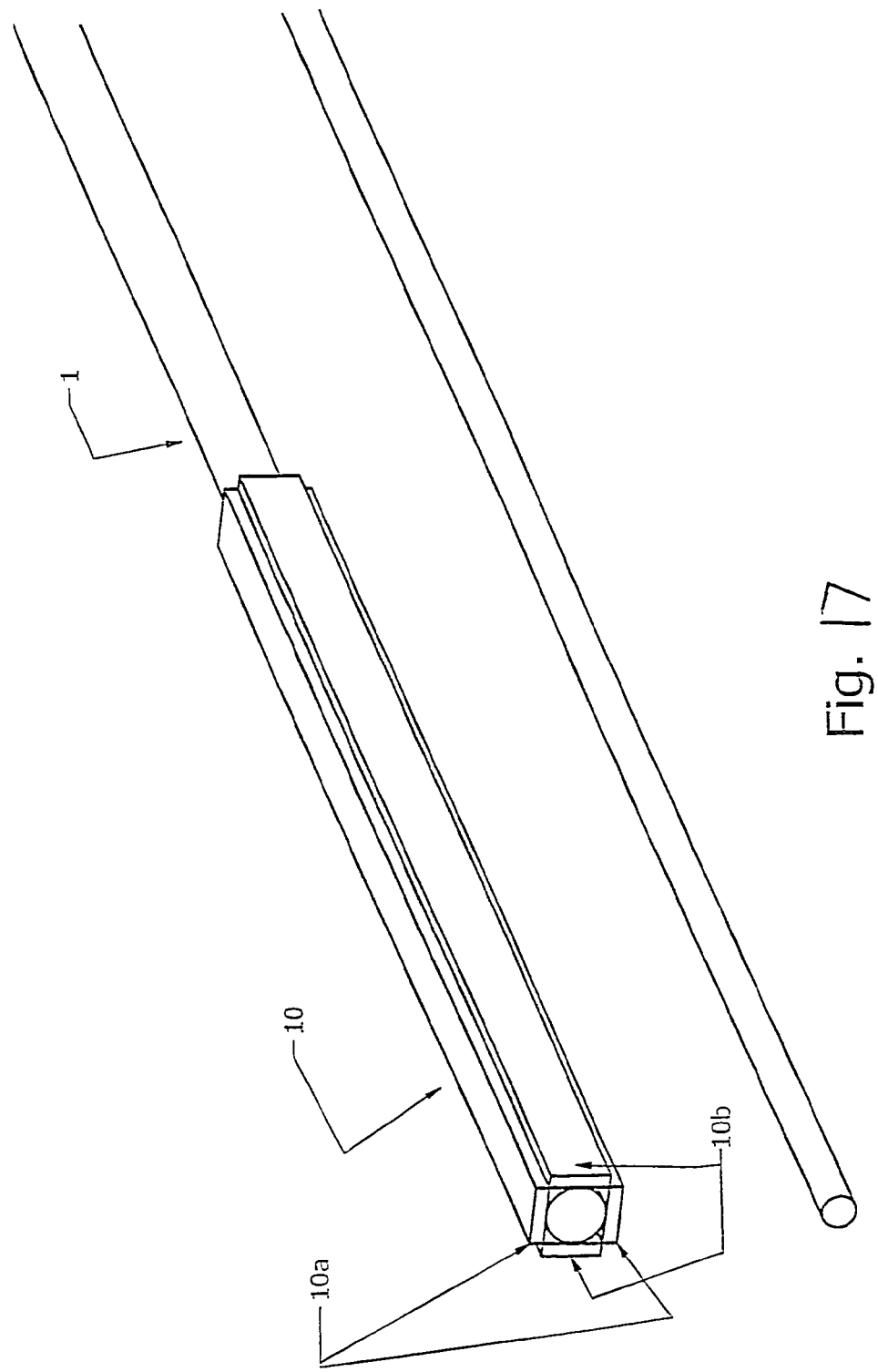
FIG. 17 shows the piezo elements in more detail.

FIG. 17 shows in greater detail the four piezo elements 10 surrounding the fiber 1. (Where is this Figure) Opposing piezo-electric element 10b are driven at the higher frequency but at opposite phase to cause the rotation of the mirror. Opposing piezo-electric elements 10a are driven at the lower frequency, but out of phase, to cause the fiber to sway in the opposite direction.

Feedback is often required in imaging systems to provide knowledge of the position of the rastering laser beam. In the systems of FIGS. 4A, 4B, 16 and 17, additional feedback piezo elements can be attached to the fiber. Movement of the fiber will move the feedback piezo-electric elements and by measuring the voltage across them provides indication of the fiber's position.

In addition to being used as a mechanical structure, a fiber can also be used to carry light and thus conduct optical signals, providing that it is made from a suitable optical material, such as glass or transparent plastic. In this case, if the end of a fiber is excited into oscillation, said fiber may serve as a scanning arrangement. It should be noted that both the laser beam, the light reflected from the inspection area, or both can be carried by optical fibers. It is also possible to have the laser beam and the light reflected from the inspection area to move through the same optical fiber in opposite directions.

Figure 18:
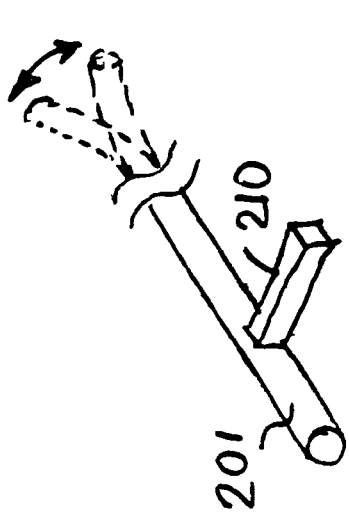
FIG. 18 shows an alternative embodiment of the piezo elements.

In one possible arrangement, the piezo-electric elements 210 can be attached to fiber 201 transversely, as depicted on FIG. 18. A piezo-electric element's alternative expansions and contractions induce oscillations of the distal end of the fiber. If the excitation frequency is close to the principal resonant frequency of the fiber, the amplitude of the fiber oscillations can be sufficient to raster over the inspected area.

Figure 19:
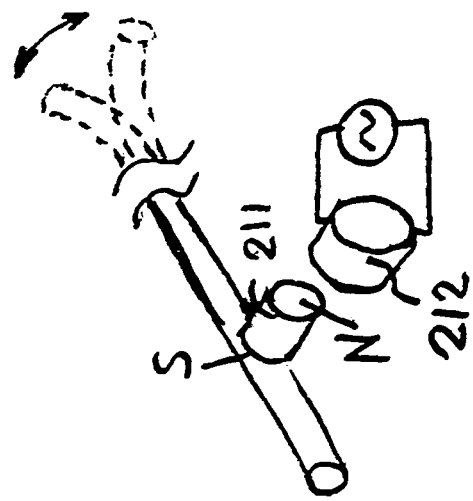
FIG. 19 shows the use of permanent magnets on the fiber.

Alternatively, the oscillations can be excited by a permanent magnet 211, which is attached to the fiber and is subjected to variable magnetic field generated by the coil 212, as depicted on FIG. 19.

Figure 20:
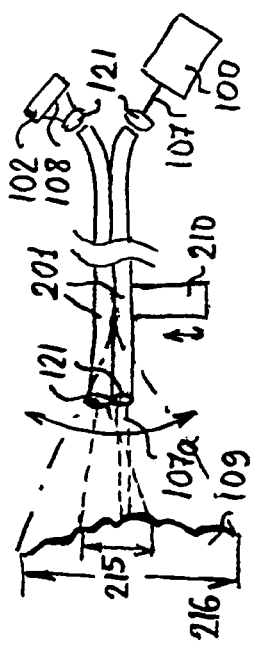
FIG. 20 shows an arrangement for limiting the Field of View of the light detector.

Generally, the light detector of the laser camera is exposed to the light reflected from the whole of the inspected area covered by the rastering laser beam. However, in some cases it might be advantageous to limit the Field of View (FOV) of the light detector to a smaller area 215, which does not cover the whole of the inspected area 216, as illustrated by FIG. 20. In this case, to insure that the light reflected from the inspected area can always reach the light detector, the FOV of the detector needs to move synchronously with the laser beam. This might be accomplished by directing the reflected light through a separate scanning arrangement, which is synchronized with the scanning arrangement for the laser light. Alternatively, the same scanning arrangement may be used for both rastering laser beam and reflected light. FIG. 20 further illustrates this principle, as two optical fibers 201, one carrying the laser beam 107 and the other the reflected light 108, are mechanically joined together and made to oscillate together due to excitation provided by the piezo-electric element 210. Respectively, the detector FOV(Field of View) 215 moves together with the scanned laser beam 107a and always overlaps it.

Further miniaturization of an endoscope can be achieved if the scanning arrangement is moved to the proximal end of the endoscope as well, so no mechanical or electrical elements is left at the distal end and light is the only media travelling through the connecting member. It is worth noting, that all-optical image transmission through an optical fiber has been eluding scientists and engineers for decades. While conceptual ideas exists, a practical solution is yet to be developed. Consequently, the flexible endoscopes (more about rigid endoscopes below) today use either a bundle of optical fibers, each responsible for a single pixel of the image, which increases the thickness of the endoscope and limit the image resolution, or use a camera at the distal end of the endoscope.

Figure 21:
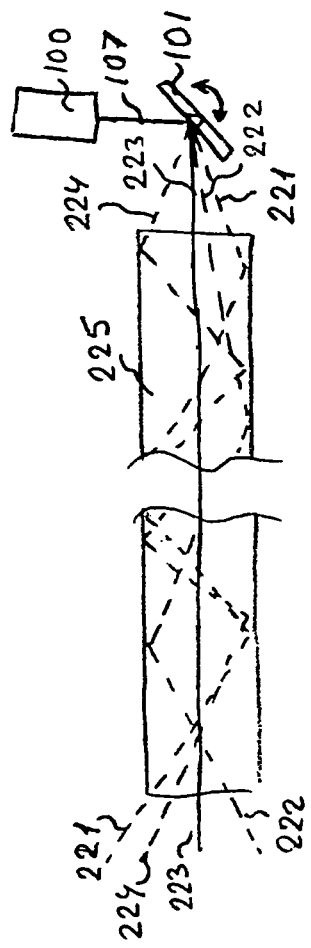
FIG. 21 shows the light rays emanating from the scanning arrangement.

The principle problem complicating the image transmission through an optical fiber is a variable number of bounces from the boundary of the fiber each ray can go through, depending on its angle of incidence. Respectively, the rays emanating from the same point may not end up in the same point or in the same order on the opposite end of the fiber, thus scrambling the transmitted image. However, for a laser camera this problem is manageable, as illustrated by FIG. 21. While the rays 222 to 224, emanating from the scanning arrangement 101, reach the end of the fiber 225 in chaotic order, each of those rays would still illuminate a distinct point on the inspected area (not shown). The light reflected from each of those points can still be detected and recorded, and the order in which the rays are reaching the inspected area, while chaotic, is repeatable from scan to scan, so the record of the reflected light can be restored into a meaningful image of the inspected area.

Figure 22:
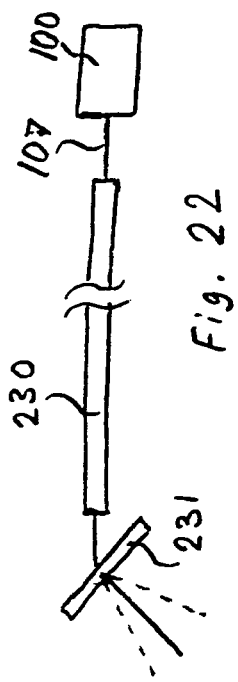
FIG. 22 shows an arrangement where a laser of variable wavelength is used.

Other methods of endoscopic all-optical image collection can be enabled as well with the laser camera. FIG. 22 depicts an arrangement where the laser 100 of variable wavelength is used, and its wavelength is changed continuously. A grating 231 at the distal end of the fiber 230 translates wavelength change into a change of the angle at which the beam propagates, thus scanning the inspected area. In this arrangement, the fiber 230 can be a single-mode fiber.

Figure 23:
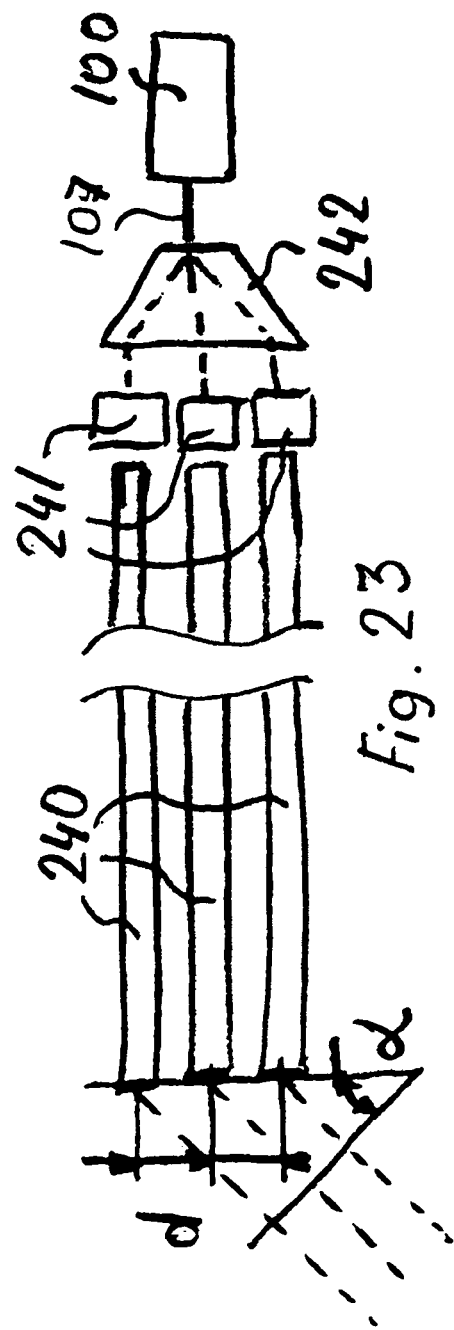
FIG. 23 shows an arrangement where the laser beam is split into several sub beams.

Another arrangement is shown on FIG. 23, where the laser beam 107 is split into several sub-beams. Each of those sub-beams is directed through a controllable delay element 241 and then on into one of the optical fibers 240, which may also be single-mode fibers. Assuming that each subsequent delay element 241 increases the delay into a respective fiber by an equal interval $\Delta t$, the resultant output beam emanating from the distal end of the fibers will be deflected by an angle $\alpha$, $\alpha \approx c*\Delta t/d$, where c is the speed of light and d is the distance between adjacent fibers.

Figure 24:
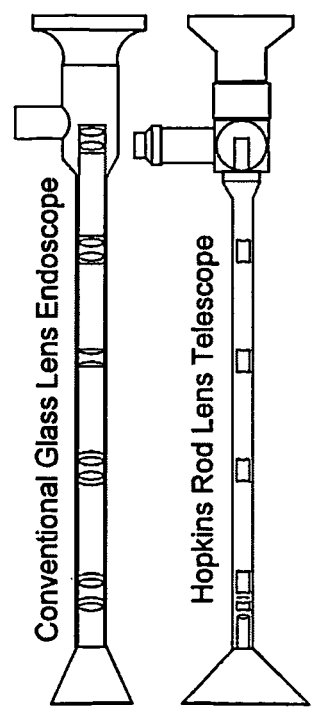
FIG. 24 shows a prior art rigid endoscope.

An important class of endoscopes are rigid endoscopes depicted on FIG. 24 (Prior Art, from http://www.vet.uga.edu/mis/img/equipment/exotics/image003.jpg). In those, the image is optically relayed from the distal to the proximal end through a system of lenses, usually, so-called Hopkins Rod Lenses. The laser camera, positioned entirely at the proximal end can be used in this class of endoscopes as well, instead of a conventional imaging camera or an optical eye piece. Additionally, the laser camera can be used without any relay lenses, assuming that the connecting piece of the endoscope is tubular and possesses a smooth reflective inner surface. In this case, the laser light can travel through it in a way similar to traveling through optical fiber, as illustrated on FIG. 21 and discussed above.

In a previous disclosure, laser imaging systems were described which are multispectral. Such multispectral techniques can be applied to the endoscope described herein. Further, in previous disclosures we described a closed loop laser imaging system which is capable of capturing images with very high dynamic range. Such techniques can be applied to the endoscope described herein. Finally, trans-illumination has been previously described and can be applied to the endoscope described herein.

While the term endoscope has been used herein, it is understood that the approaches described herein can be applied to any type of instrument wherein a laser fiber is used for connecting imaging capture electronics over a distance to a remote location, such as, remote material inspections, other medical procedures, etc.

We claim:

1. A two-dimensional scanning arrangement for a laser vein-illumination device comprising:
   a) a base;
   b) a frame, connected to said base using at least two flexible hinges, said hinges allowing the frame to move angularly with respect to the base in a first direction, said two hinges being conductive and configured to carry electrical signal;
   c) a permanent magnet rigidly attached to the frame and a coil in close proximity to the magnet, the electric coil configured to create a variable magnetic field around the magnet, to cause the magnet to generate a torque to drive angular oscillations of the frame at or near said frame's resonant frequency;
   d) an elastic torsional element, said torsional element comprising a glass fiber having a proximal end rigidly attached to said frame and a distal end rigidly attached to a mirror, and said torsional element allowing said mirror to move angularly with respect to the frame in a second direction, generally perpendicular to the first direction;
   e) a piezo-electric element mounted near said proximal end of said torsional element, the piezo-electric element configured to be excited by an electrical signal to drive angular oscillations of the mirror; and
   d) wherein the electric coil and magnet are further configured to alternate between a drive state and a feedback state to derive positional feedback of the frame oscillations, where no external voltage is applied to the coil during said feedback state, and where external voltage is applied to the coil during the drive state for the magnet to generate the torque for the driven frame oscillations; and wherein said feedback state and said drive state have variable or non-periodic durations.

2. The arrangement of claim 1, wherein said elastic torsional element is excited in a resonant node higher than fundamental.

3. The arrangement of claim 1, wherein said elastic torsional element carries a permanent magnet attached to it and a coil is placed in close proximity to said magnet.

4. The arrangement of claim 3, where said coil and magnet are is used for driving the mirror oscillations.

5. The arrangement of claim 4, where said coil and magnet are used for positional feedback of the mirror oscillations.

6. The arrangement of claim 5, the coil-magnet system has a feedback state, during which no external voltage is applied to the coil and a drive state, during which the external voltage is applied to the coil.

7. The arrangement of claim 3, where said coil-magnet system is used for deriving the positional feedback of the frame oscillations.

8. The arrangement of claim 1, where a piezo-electric element is attached to the proximal end of the elastic torsional element.

9. The arrangement of claim 1, where the axis of rotation of the mirror in the second direction passes through the center of the mirror.

10. The arrangement of claim 1, where said coil-magnet system is used for driving the frame oscillations.

11. The arrangement of claim 1, where said coil-magnet system is used for deriving a positional feedback of the frame oscillations.

12. An arrangement for moving a scanning mirror about two perpendicular axes comprising:
   a base;
   a frame;
   at least one hinge configured to connect said frame to said base, to permit said frame to move angularly with respect to said base about a first axis; said at least one hinge configured to be conductive to carry electrical signals;
   a permanent magnet fixedly secured to said frame and an electric coil in proximity to said magnet, said electric coil configured to create a variable magnetic field around said magnet, to cause said magnet to generate a torque to drive said frame to oscillate about the first axis, at or near a resonant frequency of said frame;
   a mirror;
   an elastic torsional element, said torsional element comprising a proximal end fixedly secured to said frame, and a distal end fixedly secured to said mirror, and said torsional element configured to allow said mirror to move angularly with respect to said frame about a second axis, the second axis substantially perpendicular to the first axis;
   a piezo-electric element mounted near said proximal end of said torsional element, said piezo-electric element configured to be excited by an electrical signal to create angular oscillations of said mirror;
   wherein said electric coil and magnet are further configured to alternate between a drive state and a feedback state to derive positional feedback of said frame oscillations, where no external voltage is applied to said coil during said feedback state, and where external voltage is applied to said coil during said drive state for said magnet to generate the torque for said driven frame oscillations.

13. The scanning arrangement of claim 12 wherein the electrical signal is at a frequency equal to the frequency of the torsional resonance of said elastic torsional element and mirror.

14. The scanning arrangement of claim 13 wherein said at least one hinge is configured so that a resonant frequency of said oscillating frame is approximately equal to a desired frequency of oscillation of said mirror about the first axis.

15. The scanning arrangement of claim 14 wherein the second axis passes through a center of said mirror.

16. An arrangement for moving a scanning mirror about two perpendicular axes comprising:
   a base;
   a frame;
   at least one hinge configured to connect said frame to said base, to permit said frame to move angularly with respect to said base about a first axis; said at least one hinge configured to be conductive to carry electrical signals;
   means to excite angular oscillations of said frame at or near a resonant frequency of said frame;
   an elastic torsional element, said torsional element comprising a proximal end fixedly secured to said frame, and a distal end fixedly secured to a mirror, and said torsional element configured to allow said minor to move angularly with respect to said frame about a second axis, the second axis substantially perpendicular to the first axis;

means to excite angular oscillations of said mirror;
wherein said means to excite angular oscillations of said frame is further configured to alternate between a drive state and a feedback state to derive positional feedback of said frame oscillations, where said means to excite angular oscillations of said frame is passive during said feedback state, and where said means to excite angular oscillations of said frame is active during said drive state to cause said driven frame oscillations.

17. The scanning arrangement of claim 16 wherein said feedback state and said drive state comprise variable durations.

18. The scanning arrangement of claim 17 wherein said at least one hinge is configured so that a resonant frequency of said oscillating frame is approximately equal to a desired frequency of oscillation of said mirror about the first axis.

19. The scanning arrangement of claim 18 wherein the second axis passes through a center of said mirror.

\* \* \* \* \*